US012599400B1

(12) United States Patent
    Furman et al.

(10) Patent No.: US 12,599,400 B1
(45) Date of Patent: Apr. 14, 2026

(54) SURGICAL KIT FOR SPINAL DECOMPRESSION TO TREAT SPINAL STENOSIS

(71) Applicant: Spinal Simplicity, LLC, Overland Park, KS (US)

(72) Inventors: Nicholas J. Furman, Overland Park, KS (US); Adam Frock, Lenexa, KS (US); Christina Berels, Kansas City, MO (US); Todd Moseley, Olathe, KS (US); Colton McQuinn, Peculiar, MO (US); Melissa Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 19/311,868

(22) Filed: Aug. 27, 2025

(51) Int. Cl.
    *A61B 17/3207* (2006.01)
    *A61B 17/34* (2006.01)
    *A61B 90/00* (2016.01)
    *A61B 17/00* (2006.01)
    *A61B 17/32* (2006.01)

(52) U.S. Cl.
    CPC .. *A61B 17/320758* (2013.01); *A61B 17/3421* (2013.01); *A61B 90/03* (2016.02); *A61B 2017/00367* (2013.01); *A61B 2017/320064* (2013.01); *A61B 2090/036* (2016.02); *A61B 2217/005* (2013.01)

(58) Field of Classification Search
    CPC ............ A61B 17/3421; A61B 17/3423; A61B 17/320758; A61B 90/03; A61B 17/16; A61B 17/1604; A61B 17/1615
    See application file for complete search history.

(56) References Cited

U.S. PATENT DOCUMENTS

| | | | | |
|---|---|---|---|---|
| 4,589,414 | A | * | 5/1986 | Yoshida ......... A61B 17/320016 |
| | | | | 606/171 |
| 5,873,886 | A | * | 2/1999 | Larsen ............. A61B 17/32002 |
| | | | | 606/167 |
| D598,549 | S | | 8/2009 | Cantu et al. |
| D606,654 | S | | 12/2009 | Tran et al. |
| D611,146 | S | | 3/2010 | Way et al. |
| D620,593 | S | | 7/2010 | Tran et al. |
| D627,461 | S | | 11/2010 | Cantu et al. |
| 7,896,879 | B2 | | 3/2011 | Solsberg et al. |
| 7,942,830 | B2 | | 5/2011 | Solsberg et al. |
| 8,696,671 | B2 | | 4/2014 | Solsberg et al. |

(Continued)

FOREIGN PATENT DOCUMENTS

| | | |
|---|---|---|
| WO | 2018049078 A1 | 3/2018 |
| WO | 2025137205 A1 | 6/2025 |

*Primary Examiner* — Si Ming Ku
(74) *Attorney, Agent, or Firm* — Erise IP, P.A.

(57) ABSTRACT

A system and method for excising tissue from a stenotic spinal region is disclosed. The system may comprise a surgical kit including an access instrument, a bone reamer, a bone removal instrument, and a soft tissue removal instrument. The access device may be cannulated and utilized to achieve a path for the insertion and advancement of the other surgical instruments towards a target area, such as the interlaminar region. The bone removal and/or soft tissue removal instrument may be used at various angular orientations and depths within the lumbar region to ergonomically excise compressive features including hypertrophied ligamentum flavum. Minimally invasive and open procedures are disclosed.

20 Claims, 23 Drawing Sheets

(56) References Cited

U.S. PATENT DOCUMENTS

| | | | |
|---|---|---|---|
| 8,882,772 B2 | 11/2014 | Solsberg et al. | |
| 12,207,826 B2 | 1/2025 | Frock et al. | |
| 2007/0162061 A1 | 7/2007 | Way et al. | |
| 2007/0299459 A1 | 12/2007 | Way et al. | |
| 2008/0221383 A1 | 9/2008 | Way et al. | |
| 2009/0118709 A1 | 5/2009 | Sand et al. | |
| 2009/0143807 A1* | 6/2009 | Sand ................. | A61B 17/0218 |
| | | | 606/167 |
| 2009/0287221 A1 | 11/2009 | Sand et al. | |
| 2012/0259424 A1* | 10/2012 | Hood ................... | A61F 2/4684 |
| | | | 623/23.35 |
| 2023/0404561 A1* | 12/2023 | Dinh ................. | A61B 17/3401 |
| 2026/0007417 A1 | 1/2026 | Lore et al. | |

\* cited by examiner

700

702 — Perform epidurogram

704 — Incise patient

706 — Insert access instrument through incision to target area

708 — Remove needle from access instrument

710 — Insert bone reamer and remove bone

712 — Insert bone removal instrument and remove tissue/bone

714 — Insert soft tissue removal instrument and remove tissue

716 — Remove instruments from patient and close surgical site

800

802 — Incise patient

804 — Dilate incision

806 — Insert working channel

808 — Insert bone reamer and remove bone

810 — Insert bone removal instrument and remove tissue/bone

812 — Insert soft tissue removal instrument and remove tissue

814 — Remove instruments from patient and close surgical site

SURGICAL KIT FOR SPINAL DECOMPRESSION TO TREAT SPINAL STENOSIS

BACKGROUND

1. Field

Embodiments of the current disclosure generally relate to surgical instrumentation for spinal procedures. More specifically, embodiments of the current disclosure relate to surgical instrumentation for treating lumbar spinal stenosis via decompression involving removal of tissue and/or bone.

2. Related Art

Spinal stenosis, involving the compression of the spinal cord as the spinal canal becomes narrowed, may manifest in a myriad of physical symptoms, such as back and neck pain, as well as nerve related issues including sciatica or other numbness and tingling of the limbs. Cases of spinal stenosis often stem from overcrowding within the lumbar region, resulting from bone overgrowth and the thickening of tissues and ligaments. The hypertrophying of the ligamentum flavum is a particularly problematic cause of acquired spinal stenosis; however, it may be sufficiently treatable through decompressive spinal procedures that excise tissue at a number of orientations within the stenotic region. Current instrumentation allows for treating spinal stenosis; however, these procedures are typically performed with limited capacity for instrument orientation modification to adjust cutting and without integrated depth control features for protection of the surrounding spinal region.

Thus, what is needed is a surgical kit for decompressing the spine that comprises instrumentation that minimizes the need for continual retraction and reinsertion of the surgical instruments into the back of the patient for each orientation adjustment of the instrument. As typical decompressive procedures may be standardly invasive and may involve recovery times dictated by the trauma at the surgical site of the patient, utilizing an access instrument through which excision instruments and other surgical instruments may be percutaneously operated through may allow for a reduction in the diameter of the path for surgical instrument between an incision and the target treatment area. Additionally, the access instrument, along with the orientation control of the inserted excision instrument, may minimize the quantity of required instrument reentry to achieve sufficient decompression, reducing surgical site trauma and mitigating patient recovery time.

SUMMARY

Embodiments of the current disclosure solve the above-described problems and provide a distinct advancement in the art by providing systems and methods for reducing spinal stenosis via the removal of structures impacting the compression the spinal cord, such as hypertrophied ligamentum flavum, using a surgical kit as described herein. The surgical kit may include an access instrument, a bone reamer instrument, a bone removal instrument, and a soft tissue removal instrument. The bone removal instrument and the soft tissue removal instrument may be angularly adjustable to excise compressive structures at a treatment target area.

The systems described herein may enable reduction of spinal stenosis via excision of a hypertrophied ligamentum flavum, along with surrounding vertebral structure, such as the laminae. Such decompressive procedures may be done in either an open or closed decompression with the included surgical instruments of the surgical kit. The excision may also occur in a manner that mitigates potential harms stemming from advancing a device too far anteriorly in the interlaminar region via integrated depth controls on the various instruments.

In some embodiments, the techniques described herein relate to a tissue excision system for treating lumbar spinal stenosis, including: an access instrument configured to provide access to a target treatment area, including: a cannulated shaft including an elongated passage therethrough; and a needle removably inserted through the cannulated shaft to advance the access instrument through a back surface of a patient and to the target treatment area of the patient; and an excision instrument configured to be inserted through the cannulated shaft, including: a distal end and a proximal end; an elongated cutting assembly configured to excise at least one of bone or tissue from the target treatment area and including a cutting region at the distal end; a handle at the proximal end including a trigger operable by a user to actuate the elongated cutting assembly to excise tissue or bone at the cutting region; and an orientation control assembly at the proximal end including a knob coupled to a circumference of the elongated cutting assembly such that a rotation of the knob causes a corresponding rotation of the cutting region.

In some embodiments, the techniques described herein relate to a tissue excision system for treating spinal stenosis, including: an access instrument configured to provide access to an interlaminar region of a patient, including: a cannulated access portal; and a needle configured to be inserted through the cannulated access portal to advance the access instrument to the interlaminar region; an excision instrument configured to be inserted through the cannulated access portal, the excision instrument including: a distal end and a proximal end; an elongated cutting assembly including a cutting region at the distal end that is configured to excise at least one of bone or tissue from the interlaminar region; an orientation control assembly including a knob coupled to a circumference of the elongated cutting assembly such that a rotation of the knob causes a corresponding angular orientation of the cutting region; and a depth control that is adjustable longitudinally along the elongated cutting assembly to control a depth of the cutting region within the patient.

In some embodiments, the techniques described herein relate to a method for treating spinal stenosis, including: providing an access instrument including: an access portal including a cannula, the cannula further including: a shaft with an outer circumference; and an elongated passage through the shaft; providing an excision instrument including: an elongated cutting assembly including a cutting region; an orientation control assembly including: a knob coupled to a circumference of the elongated cutting assembly; and a trigger coupled to the elongated cutting assembly; advancing the access instrument into a patient and to a target area; inserting the excision instrument through the elongated passage of the access instrument to the target area; rotating the knob to adjust an angular orientation of the cutting region; and actuating the trigger to excise at least one of tissue or bone at the cutting region.

This summary is provided to introduce a selection of concepts in a simplified form that are further described below in the detailed description. This summary is not intended to identify key features or essential features of the claimed subject matter, nor is it intended to limit the scope of the claimed subject matter. Other aspects and advantages of the present disclosure will be apparent from the following detailed description of the embodiments and the accompanying drawing figures.

BRIEF DESCRIPTION OF THE DRAWING FIGURES

Embodiments of the present disclosure are described in detail below with reference to the attached drawing figures, wherein:

FIG. 5I depicts a cross-sectional view of another bone removal instrument for some embodiments;

Figures 1A, 1B:
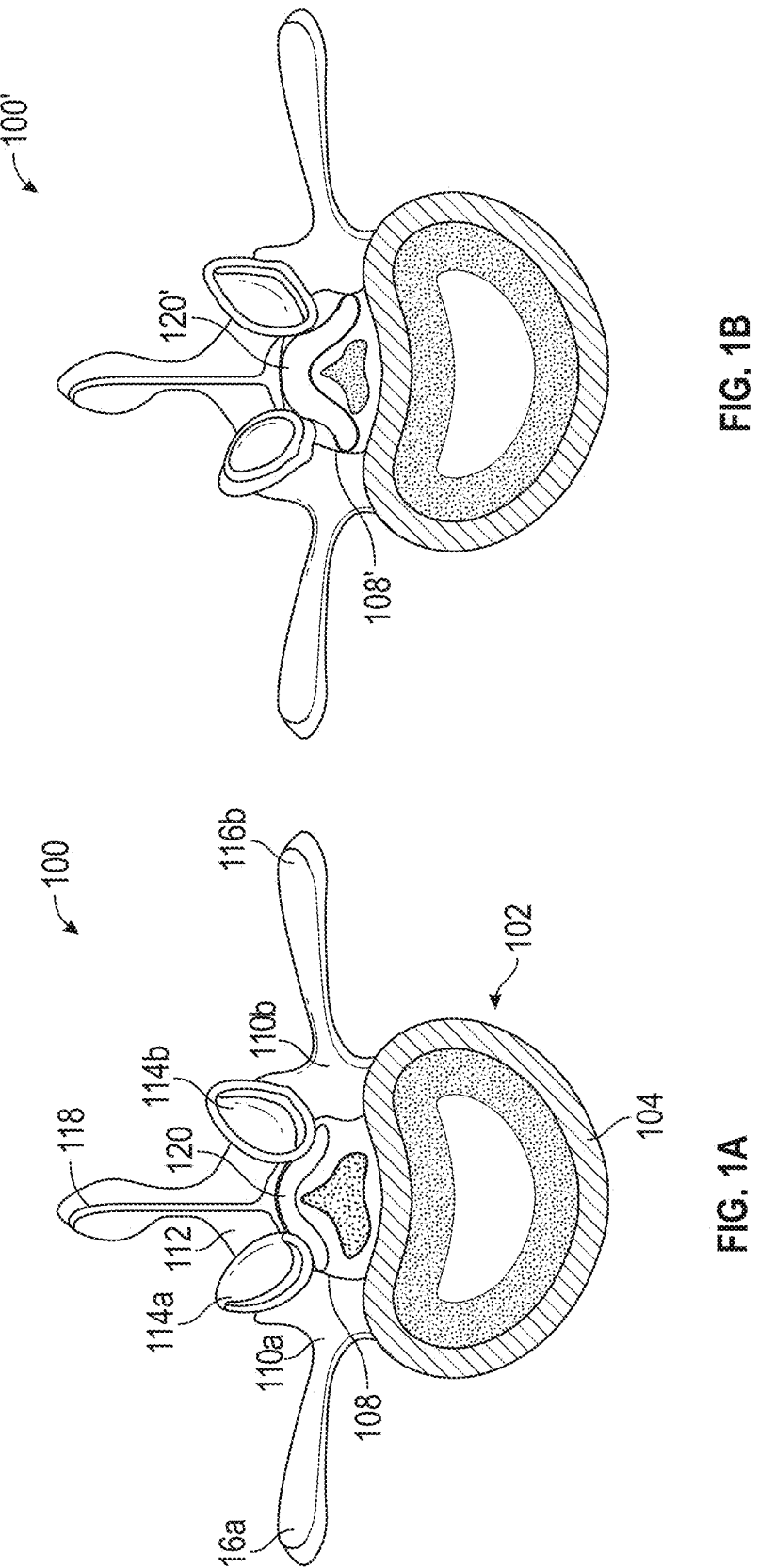
FIGS. 1A-1B depict a normal vertebra and a stenotic vertebra, respectively, for some embodiments.

The drawing figures do not limit the present disclosure to the specific embodiments disclosed and described herein. The drawings are not necessarily to scale; emphasis is instead placed upon clearly illustrating the principles of the present disclosure.

DETAILED DESCRIPTION

The following description of embodiments of the present disclosure references the accompanying illustrations that illustrate specific embodiments in which the present disclosure can be practiced. The embodiments are intended to describe aspects of the present disclosure in sufficient detail to enable those skilled in the art to practice the present disclosure. Other embodiments can be utilized, and changes can be made without departing from the scope of the present disclosure. The following detailed description is, therefore, not to be taken in a limiting sense.

In this description, references to "one embodiment," "an embodiment," "embodiments," "various embodiments," "certain embodiments," "some embodiments," or "other embodiments" mean that the feature or features being referred to are included in at least one embodiment of the technology. Separate references to "one embodiment," "an embodiment," "embodiments," "various embodiments," "certain embodiments," "some embodiments," or "other embodiments" in this description do not necessarily refer to the same embodiment and are also not mutually exclusive unless so stated and/or except as will be readily apparent to those skilled in the art from the description. For example, a feature, structure, act, etc., described in one embodiment may also be included in other embodiments but is not necessarily included. Thus, the current technology can include a variety of combinations and/or integrations of the embodiments described herein.

Generally, embodiments of the current disclosure are directed to surgical instrumentation for spinal procedures relating to the treatment of spinal stenosis. Embodiments of the present disclosure are directed toward treatments at the lumbar region of the spine, targeting intervention at individual vertebral bodies in which stenotic regions exist due to the presence of hypertrophied tissue surrounding the spinal canal. Embodiments of the present disclosure are directed toward an interventive spinal procedure for excising tissue contributing to various spinal deformities or conditions including spinal stenosis.

More specifically, some embodiments are directed to surgical instrumentation for use in procedures related to the excision of hypertrophied tissue. A surgical kit may be provided comprising an access instrument, a bone reamer instrument, a bone removal instrument, and a soft tissue removal instrument. The surgical instruments may be leveraged for percutaneous procedures for the decompression of the spinal column at a target treatment area, e.g., the interlaminar space. The interlaminar space or region is the space between adjacent, inferior and superior laminae. The access instrument may include a removable needle for piercing the skin and advancing the device to an interlaminar region of a patient. The access instrument may be cannulated for insertion of the bone reamer, bone removal instrument, and soft tissue instrument through the access instrument. The bone removal instrument and soft tissue instrument may include cutting implements at distal regions for removing bone and/or tissue. Further, each instrument may comprise an orientation control mechanism for adjusting an orientation of the cutting implement without requiring the instrument itself to be rotated.

The spinal column includes a plurality of vertebrae, five of which are considered part of the lumbar region (L1-L5). As shown in FIG. 1A, a normal vertebra 100 comprises a vertebral body 102 including the spinal disk 104 and a vertebral arch forming a perimeter around the spinal canal 108. The spinal canal 108 is a central channel providing protection to the spinal cord therewithin, further housing the dural sac (not shown) and nerves (not shown). The vertebral arch comprises a first pedicle 110a and a second pedicle 110b which extend posteriorly from the posterolateral surfaces of the vertebral body 102 and provide connection to the laminae 112 at a first facet 114a and a second facet 114b. The laminae 112 provides additional protection of the spinal cord within the spinal canal 108 and structural support of the greater vertebral column. Moreover, a first transverse process 116a, a second transverse process 116b, and a spinous process 118 extend from the laminae 112. The ligamentum flavum 120 is tissue along the anterior edge of the laminae 112 adjacent to the dural sac and corresponding nerves within the spinal canal 108. As FIG. 1A depicts a normal vertebra 100 of a patient not experiencing spinal stenosis, the normal locations and sizes, especially as they pertain to the spinal canal 108 and the surrounding ligamentum flavum 120, are reflected.

FIG. 1B depicts an exemplary vertebra of a patient experiencing spinal stenosis. Compared to the normal spinal structures, the stenotic vertebrae 100' features a constricted spinal canal 108', which causes compression on the spinal cord, leading to back pain for an individual. The constricted spinal canal 108' is stenotic as a result of the thickening of the ligamentum flavum 120 causing compression of the more anteriorly located dural sac along with nerves within. As such, reducing the thickened state of the ligamentum flavum via a surgical procedure may allow for a reduction in the compression of the spinal cord and associated symptoms including back pain, weakness, numbness, or other resulting discomfort. The spinal decompression procedures described herein may be utilized for the excision of the hypertrophied ligamentum flavum 120' contributing to the compression of spinal structures within the spinal canal 108' of patients experiencing spinal stenosis.

Surgical Kit

As discussed, embodiments of the present disclosure are directed toward a surgical kit comprising instruments utilized in percutaneous closed procedures and/or open decompression procedures to decompress the spine and treat spinal stenosis. The surgical kit may be utilized for tissue excision at the interlaminar region of the spine to reduce stenosis or other spinal conditions resulting from the hypertrophy of tissue. In some embodiments, the surgical kit described herein may be used for performing laminotomies, laminectomies, and other similar tissue and/or bone excision procedures in the lumbar spine.

In some embodiments, the surgical procedure may be performed on a patient lying prone on a surgical table and may be conducted posteriorly through the back of the patient to a target area within a stenotic region. In some procedures, this procedure will occur within the lumbar region of the spine. However, it will be appreciated that the procedure may be used to treat any stenotic region in which hypertrophied tissue contributes to stenosis or related back conditions. Such alternative regions may include the cervical region and the thoracic region.

Figure 2:
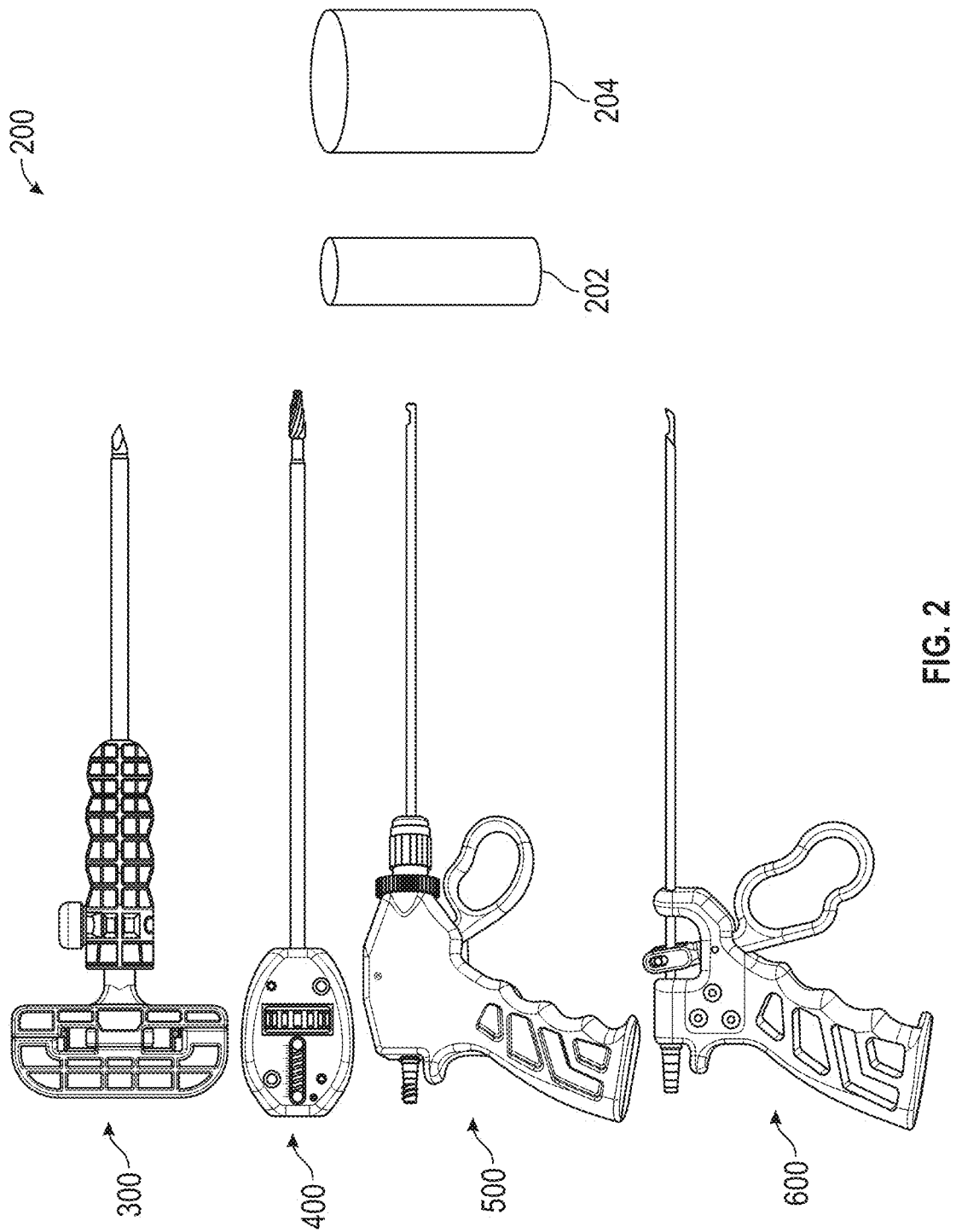
FIG. 2 depicts a surgical kit including various surgical instruments for performing a decompressive spinal procedure for some embodiments.

FIG. 2 illustrates a surgical kit 200 including a plurality of surgical instruments utilized for tissue access and excision within the spine, such as within an interlaminar region. In some embodiments, surgical kit 200 includes an access instrument 300, a bone reamer instrument 400, a bone removal instrument 500, and a soft tissue removal instrument 600.

The access instrument 300 may be configured to provide entry to the interlaminar region and may be cannulated to provide an opening or working channel for insertion of the other instruments throughout the entirety of the procedure. The bone reamer instrument 400 may be inserted through the access instrument 300 and may be utilized, as needed, for bone removal. Namely, the bone reamer instrument 400 may be utilized for the reaming of bone structure preventing sufficient access to the ligamentum flavum 120'. After bone removal with the bone reamer instrument 400, the bone removal instrument 500 may be inserted through the access instrument 300 and used to excise both bone and/or tissue, such as bone from the laminae and the ligamentum flavum tissue. Thereafter, the soft tissue removal instrument 600 may be inserted through the access instrument 300 and used to excise soft tissue, such as that from the ligamentum flavum.

In some embodiments, all the instruments 300, 400, 500, 600 are utilized in a minimally invasive decompression procedure. In such procedures, the bone reamer instrument 400, the bone removal instrument 500, and the soft tissue removal instrument 600 may be inserted into the access instrument 300 and advanced toward the interlaminar space. These instruments may be used in the order sequentially described above; however, in some embodiments, a surgeon may alternate between use of the bone removal instrument 500 and the soft tissue removal instrument 600. In some embodiments, only some of the instruments 300, 400, 500, 600 may be used. However, in minimally invasive surgical procedures such as closed laminotomies and closed laminectomies, the access instrument 300 may be required for the insertion and advancement of any other surgical instruments toward the target area of the patient. In some procedures, at least one of the bone removal instrument 500 or the soft tissue removal instrument 600 may be used in addition to the access instrument 300. In some procedures, the bone reamer instrument 400 may be utilized to establish adequate access to the ligamentum flavum preceding tissue excision, while in others the pathway from the patient's back to the interlaminar space may be relatively unobstructed such that no bone needs to be removed and the access instrument 300 can advance directly to the interlaminar space.

It will be appreciated that a myriad of factors may influence the instruments 300, 400, 500, 600 utilized for the decompression procedure. Such factors may relate to the hypertrophied state of the ligamentum flavum 120' and the surrounding environment of the patient's spine including structures hindering access to the interlaminar space or preventing adequate excision of the tissue. As such, specific instrument selection may occur at the discretion of the operating surgeon responsive to individual patient-related factors as will be appreciated by those of skill in the art. Each of the instruments 300, 400, 500, 600 are discussed in further detail below.

In some embodiments, the surgical kit 200 may further include a plurality of dilators 202 and a working channel 204 for use in an open decompression procedure. In such procedures, the plurality of dilators 202 may be of sequentially increasing diameters and configured to be inserted through an incision to dilate the incision and establish a direct and open path to the interlaminar space. Upon sufficient dilation of the incision for the open decompression, a working channel 204 (e.g., a sleeve) may be inserted into the dilated space. Resultingly, the working channel 204 may provide access through which instruments of the surgical kit 200 may be inserted into and advanced towards the interlaminar space. When an open procedure is performed, the surgeon may forego the use of access instrument 300. Both the plurality of dilators 202 and working channel 204 are discussed in further detail with respect to FIG. 8.

Access Instrument

Figure 3A:
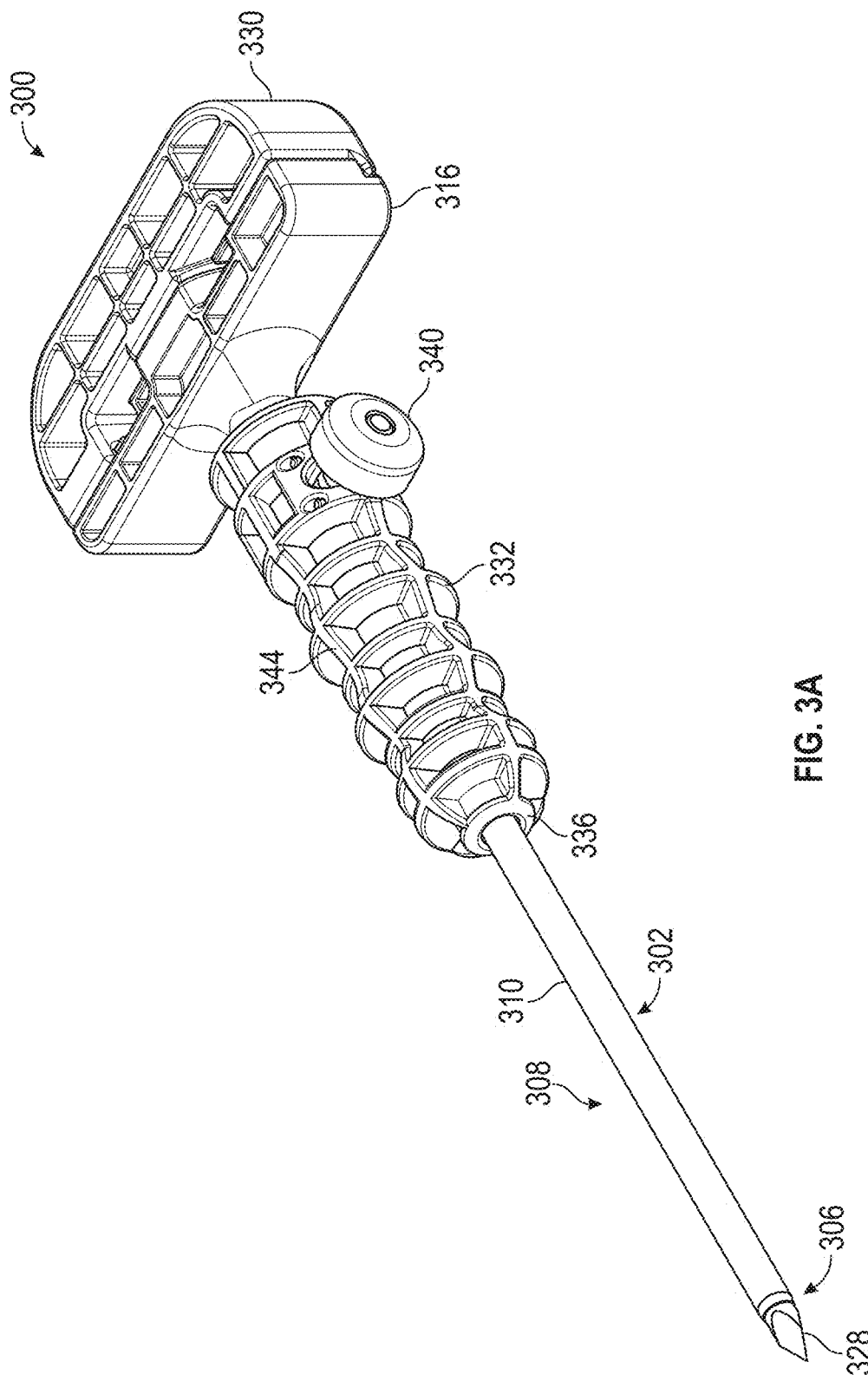
FIG. 3A depicts a perspective view of an access instrument for some embodiments.
Figure 3B:
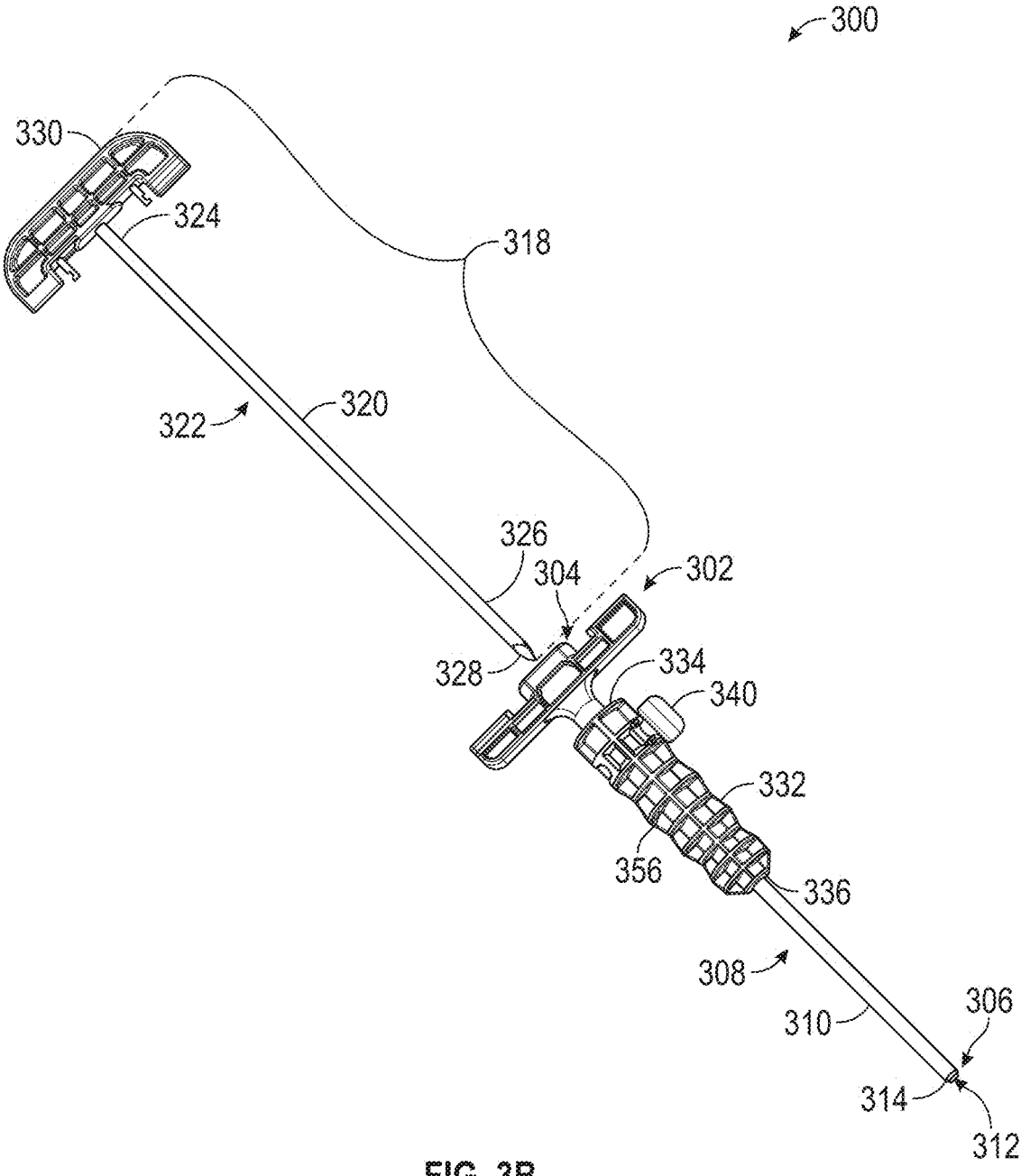
FIG. 3B depicts an exploded view of the access instrument for some embodiments.
Figure 3C:
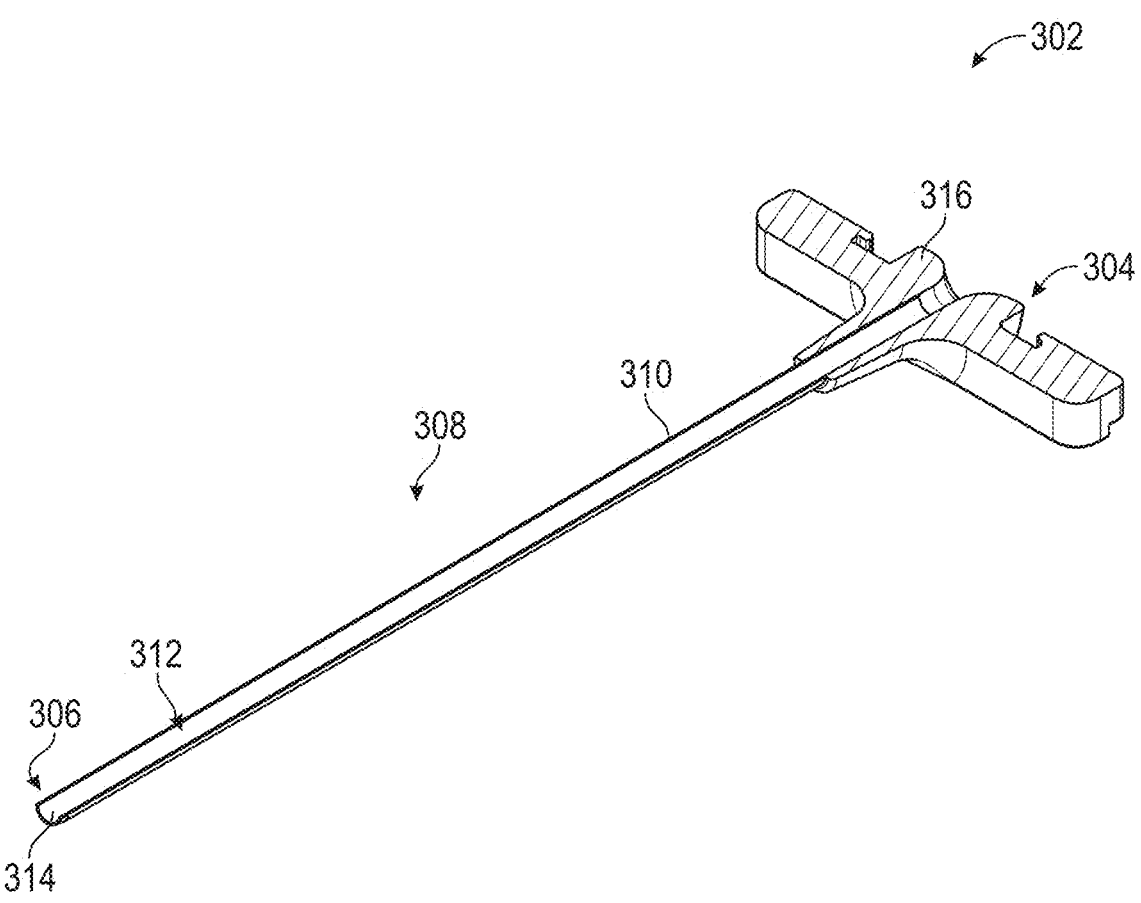
FIG. 3C depicts a cross-sectional view of the access portal for some embodiments.
Figures 3D, 3E:
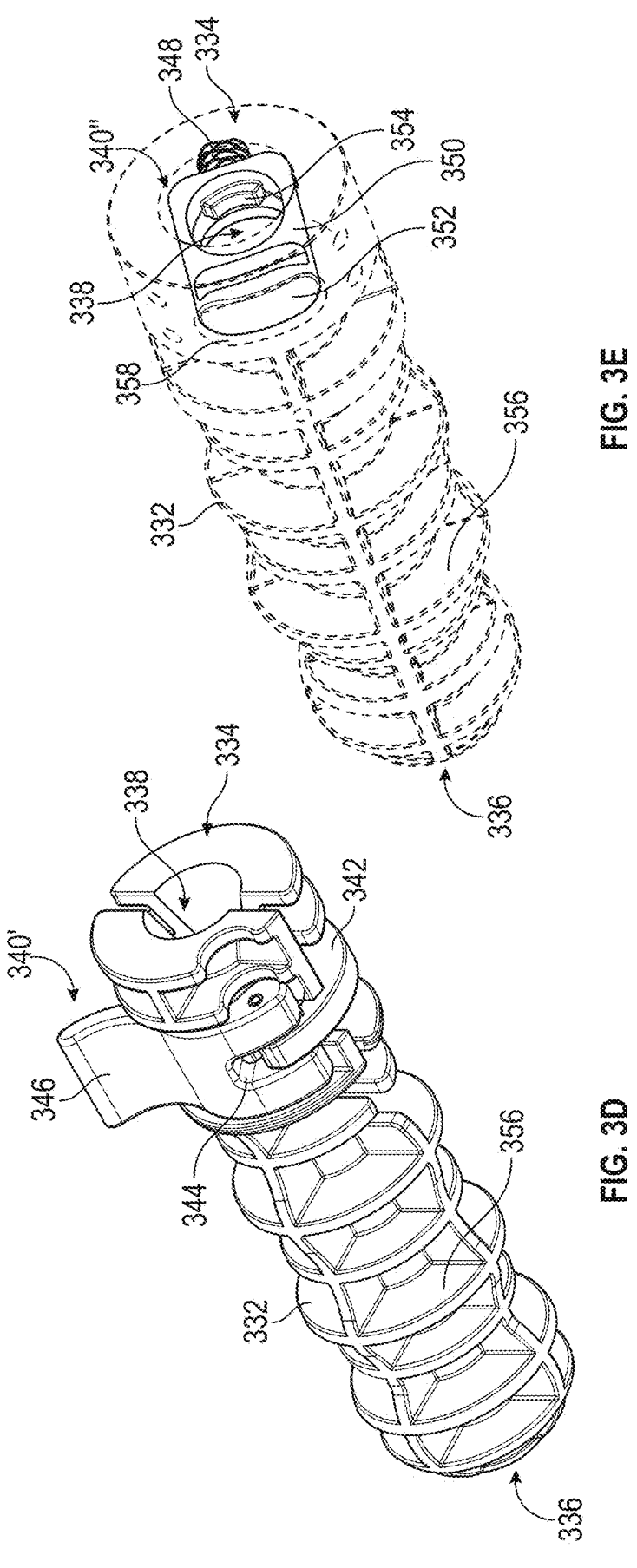
FIG. 3D depicts a perspective view of a first backstop of the access instrument for some embodiments.
FIG. 3E depicts a perspective view of a second backstop for some embodiments.

FIGS. 3A-3E depict access instrument 300 in accordance with embodiments of the present disclosure. FIGS. 3A and 3B illustrate a perspective and an exploded view, respectively, of the access instrument 300; FIG. 3C is a cross-sectional view of an access portal 302 of access instrument 300; and FIGS. 3D-3E illustrate different backstops for access instrument 300. As discussed, the access instrument 300 may be configured to be inserted into an incision at a back surface of a patient and to permit insertion of the other surgical instruments 400, 500, 600 through access instrument 300.

Referring first to FIGS. 3A-3C, in some embodiments, access instrument 300 comprises an access portal 302, which comprises a proximal portal end 304 and a distal portal end 306. The access portal 302 may further comprise a cannula 308 formed by a shaft 310 and a central passage 312 extending through the shaft 310 such that a distal aperture 314 is presented. As described herein, the various instruments 400, 500, 600 may be inserted through cannula 308, with their respective distal ends extending out of distal aperture 314 to ream bone and/or excise tissue. In some embodiments, the shaft 310 may be an elongated circular tube. However, it will be appreciated that the shape of the cannula 308 and, thus, the shape of the components of the cannula 308 (i.e., the central passage 312 and distal aperture 314) may be any shape conducive to receiving the bone reamer instrument 400, the bone removal instrument 500, and the soft tissue removal instrument 600 therethrough. As such, it is contemplated that access portal 302 may comprise various lengths and geometries (e.g., cylindrical, triangular, rectangular, etc.). The access portal 302 may be inserted by the surgeon through the back incision of a patient during a closed spinal procedure, and access portal 302 may be maintained within the patient without removal throughout the entirety of the procedure. However, it will be appreciated the surgeon may remove or otherwise adjust the location of the access portal 302 as needed throughout the procedure In some embodiments, the proximal portal end 304 may have a handle 316 disposed about the central passage 312 for the surgeon to grip during insertion and further manipulation of the access instrument 300. The handle 316 may extend laterally in two opposing directions to provide an ergonomic contact point for a surgeon to insert the access portal into the patient. In some embodiments, the handle 316 may be disposed radially about the central passage 312. In still other embodiments, the handle 316 may be asymmetrical with respect to the central passage 312. For instance, the cannula handle 316 may be an extrusion extending only one direction laterally from the central passage 312.

The access instrument 300 may further comprise a removable portion 318, and initial insertion of the access instrument 300 through the incision may be done with the removable portion 318 inserted through the access portal 302. Removable portion 318 may comprise an elongated removable rod 320 for creating a path to the target area (e.g., to a hypertrophied ligamentum flavum 120' in a stenotic region).

As shown, the removable portion 318 may comprise a needle 322 having a proximal needle end 324 and a distal needle end 326 at which a distal cutting tip 328 may be disposed to penetrate through bone (e.g., laminar structures) and/or tissue in order to reach the interlaminar space.

In some embodiments, needle 322 is a Jamshidi needle with a trocar tip as the distal cutting tip 328 such that the needle 322 is hollow with a tapered cutting edge. In some embodiments, the needle 322 may be any other needle type including, but not limited to, a Salah needle or a Klima needle. In some embodiments, removable portion 318 may not comprise a needle. For example, it is contemplated the removable portion handle 316 may comprise distal cutting tip 328 configured as a drill bit, with elongated removable rod 320 being powered by a drill to rotate the drill bit. Generally, the removable portion may comprise any medical grade device adequately sized and tapered to advance through the back of a patient and create a path to the target area for placement of the access instrument 300.

In use, the removable portion 318 may be gripped at least partially by the surgeon with one hand via a needle handle 330 at the proximal needle end 324 during the insertion of the access instrument 300, throughout the advancement of the access instrument 300 towards the interlaminar space, and for any additional manipulation of the access instrument 300 within the back of the patient during which the needle 322 may be used. The access instrument 300 may be inserted approximately perpendicular to the interlaminar space (i.e., at a 90-degree angle to the back surface), aiming superior to the inferior vertebra within the interlaminar space. Once this landmark is hit, the access instrument 300 can be angled to align with the interlaminar space between the superior and inferior laminas for insertion of the other instruments.

If the procedure involves the reinsertion of the removable portion 318 through the access portal 302 at any time following initial insertion of the entire access instrument 300, the needle 322 and, by extension, the distal cutting tip 328 may be advanced up until the point at which the needle handle 330 comes into contact with the handle 316. Once the interlaminar space is reached, the surgeon may remove the removable portion 318 from access portal 302, enabling the remaining instruments 400, 500, 600 to be inserted into access portal 302 as needed. Further, the removable portion 318 may be removed to enable insertion of bone reamer instrument 400 to ream bone as needed and then reinserted once the bone has been reamed to continue the advancement into the interlaminar space.

With additional reference to FIGS. 3D-3E, the access instrument 300 may further comprise a backstop 332 received around the circumference of the shaft 310. Backstop 332 comprises a proximal end 334 and a distal end 336. The ends 334, 336 may be flat, as shown, or may take other shapes (e.g., curved). The distal end 336 of backstop 332 may be configured to rest against the patient's back during the surgery. Backstop 332 may be adjustable longitudinally along shaft 310 to control a depth the instruments 400, 500, 600 and the needle 322 are insertable into the patient. Sliding backstop 332 distally along shaft 310 will decrease the depth reachable by the other instruments, while sliding backstop 332 proximally along shaft 310 will increase the depth reachable by the other instruments. The backstop 332 may be gripped by the surgeon throughout the procedure to maintain the orientation of the central passage 312 to the target area throughout tissue excision.

In some embodiments, the backstop 332 may comprise grooves 356 disposed radially along the circumference and configured for improved ergonomics for the operating surgeon. The grooves 356 may be sized and spaced for the surgeon to place a finger between adjacent grooves 356 In some embodiments, the backstop 332 may have grooves 356 disposed in various configurations while still improving the ergonomic feature of the backstop 332 as a gripping feature (i.e., perpendicular grooves, vertical grooves, horizontal grooves, etc.).

In some embodiments, the backstop 332 may comprise a passage 338 extending from the proximal end 334 to the distal end 336. The backstop 332 may be adjustably received at the external circumference of the shaft 310 via the passage 338. Namely, the backstop 332 may be adjustably coupled to the shaft 310 by a locking mechanism 340 such that the depth at which the instruments 300, 400, 500, 600 may be inserted into the back of the patient may be modified throughout the procedure as discussed above. FIG. 3A illustrates a first locking mechanism 340, while FIGS. 3D and 3E illustrate a second locking mechanism 340' and a third locking mechanism 340", respectively.

As shown in FIG. 3A, in some embodiments, the first biasing mechanism 340 may comprise a knob rotatable to tighten a collar (not shown) of the backstop 332 around the outer circumference of the shaft 310. The collar may be tightened via rotation of the knob to secure backstop 332 to shaft 310 and loosened to decouple the collar from the shaft 310 for adjusting the position of backstop 332. In some embodiments, an O-ring may be added to the backstop 332 to ensure equal pressure distribution around the circumference of the shaft 310 and to prevent damage resulting from a concentrated force applied by the backstop 332 to the shaft 310. During some procedures, it may be desirable to selectively couple the backstop 332 along the shaft 310 at a distance such that the distal end 336 is flush with the back surface of the patient. In other procedures, or at another point in the same procedure, the backstop 332 may be coupled to the shaft 310 such that the distal end 336 is positioned some offset distance from the back of the patient. As the backstop 332 may define the distance the cannula 308 is advanced within the back of the patient, the backstop 332 may also dictate the allowable anterior advancement of the needle 322 and the distal ends of instruments 400, 500, 600. The position of the backstop 332 and any changes to this position may be determined by the surgeon and informed by the spinal structures of each patient.

Looking now at FIG. 3D, backstop 332 is illustrated with a second locking mechanism 340' for some embodiments. As shown, second biasing mechanism 340' may comprise an integrated cam lock 342 housed within a partial slit 344 of the backstop 332. The partial slit 344 may be disposed laterally on the body of the backstop 332. In some embodiments, the cam lock 342 may comprise a hinged switch 346 extending from the cam lock 342. In some embodiments, the hinged switch 346 may be engaged to secure the backstop 332 to the shaft 310. Specifically, the hinged switch 346 may be actuated to move the cam lock 342 within the partial slit 344 at the inner surface of the passage 338, effectively closing the partial slit 344. When the partial slit 344 is closed, the backstop 332 may tighten along the shaft 310 to lock the backstop 332 into place.

Turning now to FIG. 3E, in some embodiments, the backstop 332 may comprise a spring-loaded locking mechanism 340". In FIG. 3E, the backstop 332 is shown in dashed lines to represent a transparent view so that the internal components of the spring-biased locked mechanism 340" are viewable. The spring-loaded locking mechanism 340" may comprise an internal spring 348, a collar 350 comprising a button 352 and an abutting surface 354, which are separated by passage 338. That is, the collar 350 may comprise a central void concentric with the passage 338. The button 352 may be accessible via an opening 358 of the backstop 332 to be depressed by a surgeon. In some embodiments, the internal spring 348 may extend from an internal side of the button collar 350 opposite of the opening 358. The spring 348 may be disposed within the backstop 332 and sandwiched between the collar 350 and an outer face of the backstop 332. Accordingly, when the button 352 is manually depressed by the surgeon, the internal spring 348 may be compressed such that the abutting surface disengages with the shaft 310, thereby enabling the surgeon to adjust the longitudinal position of the backstop 332. When the button is released, the spring 348 may be biased to expand to engage the abutting surface to lock against the shaft 310. As such, the spring-loaded locking mechanism 340" may lock the backstop 332 into place along the shaft 310 after positioning at a desired location.

Various other locking mechanisms for coupling the backstop 332 to the shaft 310 are contemplated. For example, a backstop 332 with a tightening screw or a detachable quick release pin are contemplated.

Bone Reamer Instrument

Figure 4A:
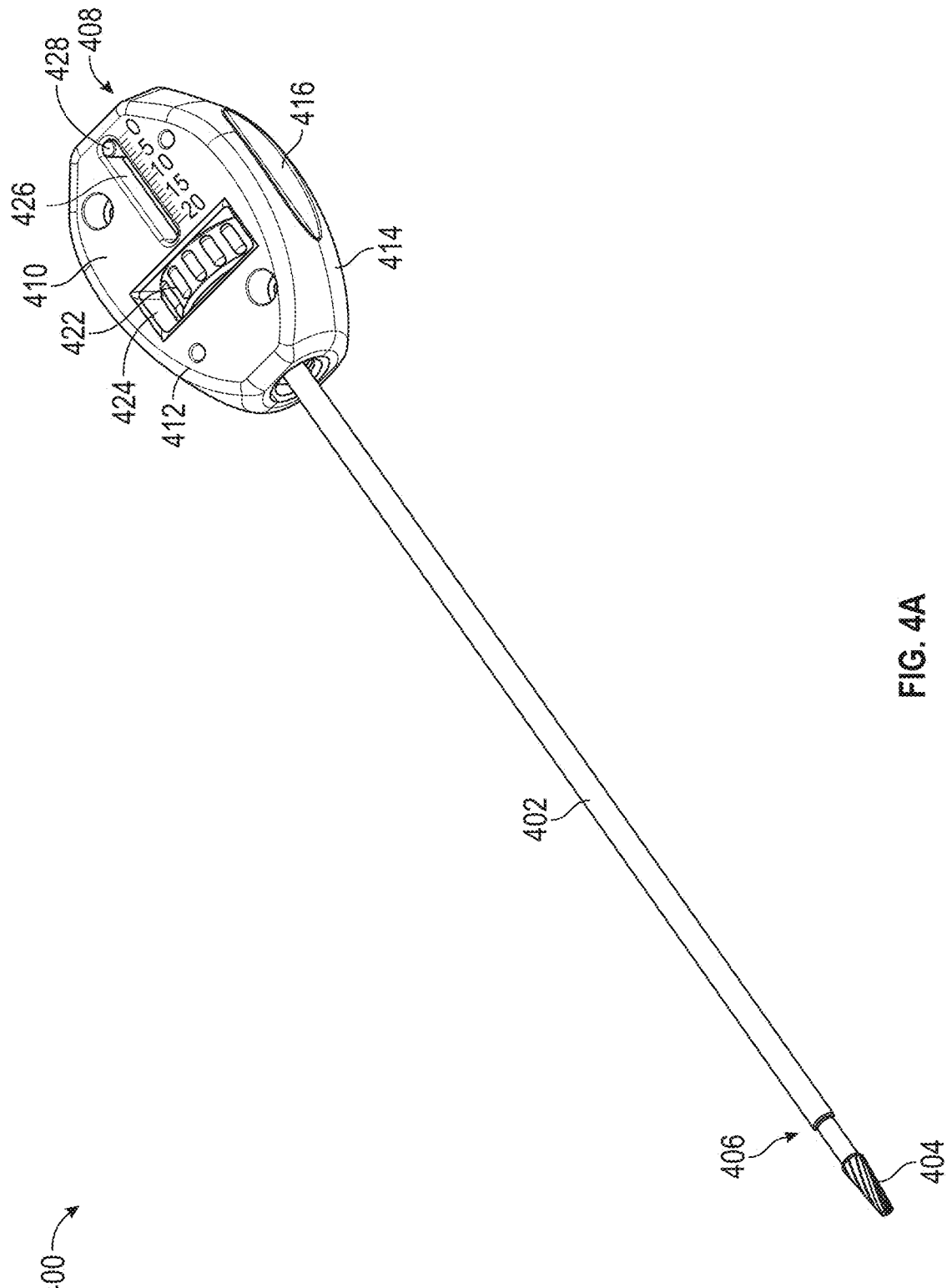
FIG. 4A depicts a perspective view of a bone reamer for some embodiments.
Figure 4B:
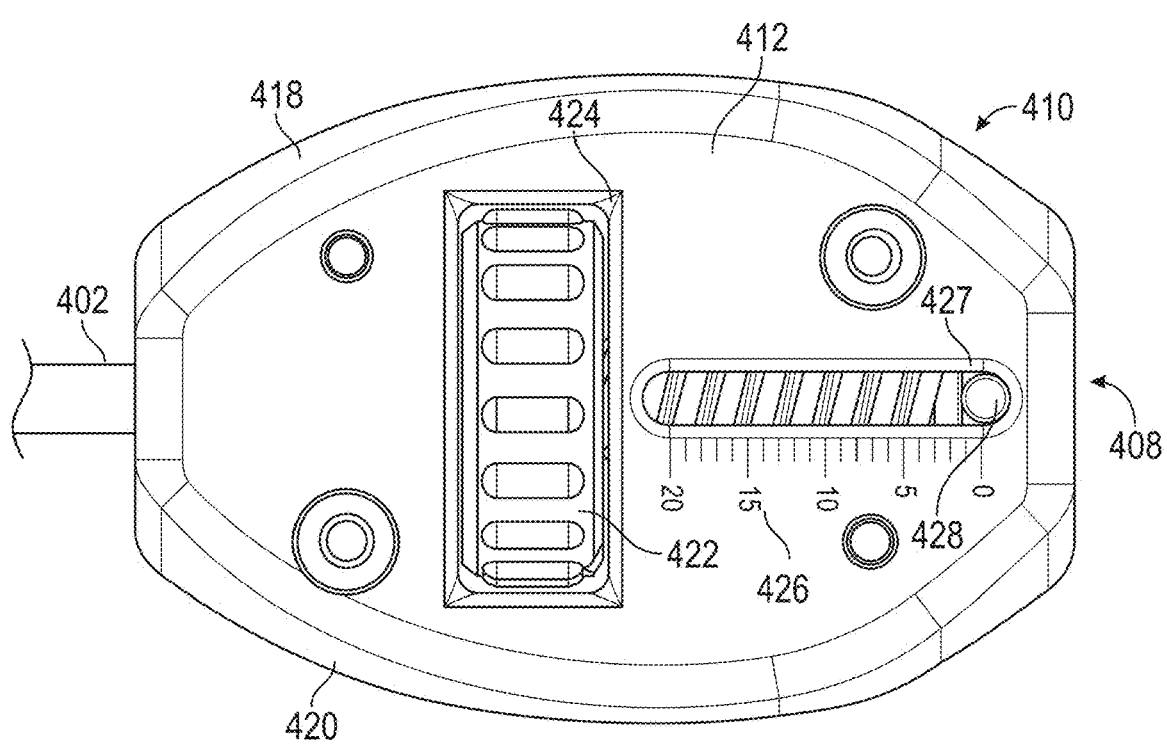
FIG. 4B depicts a close-up view of a proximal end of the bone reamer for some embodiments.
Figure 4C:
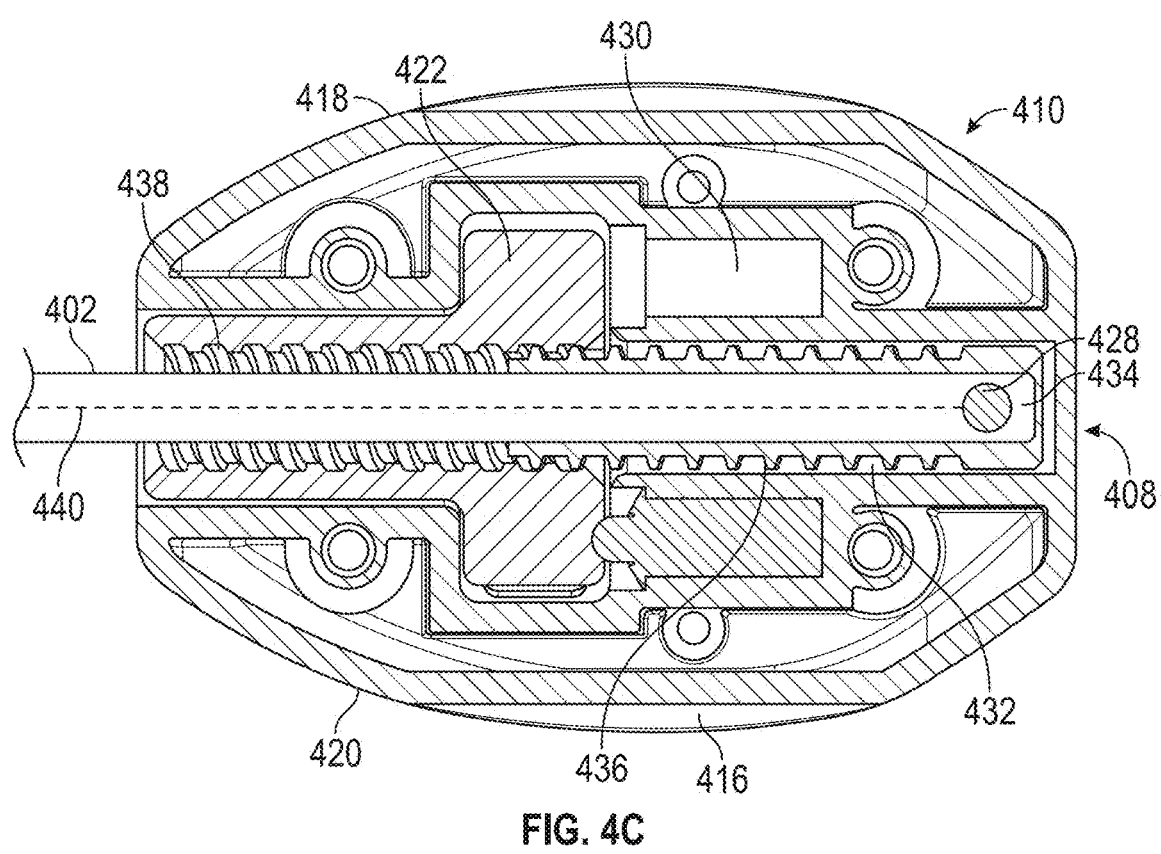
FIG. 4C depicts a cross-sectional view of the close-up view of the bone reamer for some embodiments.

Turning now to FIGS. 4A-4C, bone reamer instrument 400 is depicted for some embodiments. FIG. 4A is a perspective view of bone reamer instrument 400; FIG. 4B is a close-up view of a proximal end of bone reamer instrument 400; and FIG. 4C is a cross-sectional view of FIG. 4B.

In some embodiments, the bone reamer instrument 400 may comprise an elongated rod 402 with a distal reaming tip 404 at a distal end 406 of bone reamer instrument 400. In some embodiments, the distal reaming tip 404 may be configured as a burr to ream holes in the bone that otherwise prevent sufficient access to the ligamentum flavum. In some embodiments, the distal reaming tip 404 is tapered or may have other geometries. Such reaming may be especially useful where the laminae is shingled, which may prevent direct access by the needle 322 to the interlaminar space.

Bone reamer instrument 400 may further comprise a proximal end 408 comprising a housing 410 for the surgeon to grasp to manipulate the bone reamer instrument 400. Housing 410 may function as a handle for manipulating the bone reamer instrument 400. In some embodiments, the housing 410 may be formed of two injection molded halves 412, 414 surrounding the elongated rod 402. In some embodiments, the housing 410 may be a singular piece constructed as a unitary extruded feature. The housing 410 may be constructed of plastic, such as those used for medical devices not inserted within the body (e.g., polypropylene, polyethylene, polycarbonate, etc.), high-performance polymers, or metals (e.g., stainless steel, aluminum, etc.).

In use, the surgeon may insert the bone reamer instrument 400 and rotate the housing 410 to rotate distal reaming tip 404 to ream holes in hindering bony structures using one hand while the other hand continues to maintain its hold on the backstop 332 of the access instrument 300. As such, the housing 410 may further comprise grip features 416 for gripping the housing 410 during surgeon manipulation of the bone reamer instrument 400 including for insertion into the access portal 302 and rotation of the distal reaming tip 404 via rotation of the housing 410. The housing 410 may be coupled about the elongated rod 402 such that rotation of the housing at the grip features 416 rotates the elongated rod 402 and, thus, the distal reaming tip 404. Thus, rotation of the housing generates bone reaming. In some embodiments, the grip features 416 may be included on both a first side 418 and a second side 420 of the housing 410. In some embodiments, the grip features 416 may be elongated oval indentions along the housing 410; however, it will be appreciated that the grip features 416 may be indentions of any shape conducive to improving surgeon grip along the bone reamer instrument (i.e., circular, trapezoidal, rectangular, etc.). In some embodiments, the grip features 416 may be a plurality of indentions such that each of the plurality of indentions may accommodate one finger of the surgeon at various locations about the housing 410. Other grip features 416 such as bumps, knurls, or other protrusions are contemplated.

FIGS. 4B and 4C depict various external and internal features of the proximal end 408, respectively, including features contributing to depth control of distal reaming tip 404, as discussed below. The initial depth to which the bone reamer instrument 400 may be advanced through access instrument 300 and into the back of the patient (i.e., within the interlaminar space) may depend on the location at which the backstop 332 is selectively coupled to the shaft 310. Thus, the bone reamer instrument 400 may have an initial depth control as the bone reamer instrument 400 is manually advanced by the surgeon through the access portal 302 until a distal end of the housing 410 contacts the top of the handle 316 (when removable portion 318 is removed, handle 316 may form the proximal surface of access instrument 300). In some embodiments, bone reamer instrument 400 additionally comprises an integrated depth control mechanism to allow for further adjustment of the bone reamer instrument 400 depth, namely the depth of distal reaming tip 404, within the patient.

As seen in FIG. 4B, the depth control mechanism may include a knob 422, which may be disposed in a window 424 extending fully through the housing for access by the surgeon. In some embodiments, the window 424 may extend through shaft 310 such that knob 422 is accessible from both the first housing half 412 and a second housing half 414. The knob 422 may comprise various ridges for ease of rotation. The knob 422 may be coupled to the elongated rod 402 such that knob 422 may be rotated in a first direction (e.g., clockwise) to advance elongated rod 402, and therefore, distal reaming tip 404, anteriorly (distally) beyond its initial depth. Likewise, knob 422 may be rotated in a second direction opposite the first direction (e.g., counterclockwise) to retract the distal reaming tip 404 posteriorly (proximally). Notably, in some embodiments, the elongated rod 402 may be moved by the knob 422 to adjust the depth of distal reaming tip 404 wholly independent from manual rotation of the entire bone reamer instrument 400 by the surgeon at the housing 410. Such separation of rotation elements may allow for both improved access to the hypertrophied ligamentum flavum through the removal of additional interfering structures by advancing the cutting point further anteriorly and through the mechanically integrated depth control of the anterior extension.

The depth of the bone reamer instrument 400 beyond the initial depth is indicated by a ruler 426 externally formed along a slot 427 of the housing 410 (FIG. 4B). More specifically, the ruler 426 provides a visual indicator of the bone reamer instrument 400 depth in millimeters as set by the rotation of the knob 422 that enables movement of the distal reaming tip 404 anteriorly beyond the initial depth. Each housing half 412, 414 may comprise ruler 426 and/or slot 427, or ruler 426 and/or slot 427 may only be disposed on one half 412, 414.

To effectuate the longitudinal adjustment of distal reaming tip 404 via the depth control mechanism, bone reamer instrument 400 may further comprise a pin 428 coupled to a proximal end of the elongated rod 402 and extending through slot 427. Thus, the movement of the elongated rod 402 using the knob 422 causes a corresponding movement of the pin 428, providing a visual indicator to the surgeon of the change in depth of distal reaming tip 404. Providing such an indicator for fine control over the depth of the distal reaming tip 404 is beneficial because it is possible to pierce the ligamentum flavum and damage the critical neural structures that are located anteriorly relative to the ligamentum flavum. Thus, the visual indication can prevent the surgeon from advancing the distal reaming tip 404 too far anteriorly.

The pin 428 may also provide a mechanical stop against the distal surface of slot 427 to prevent further extension of distal reaming tip 404 anteriorly (distally). Thus, the distal end of ruler 426 may correspond to the furthest extension of distal reaming tip 404 the initial depth. In some embodiments, the ruler 426 may have measurement increments ranging from 0 to 20 millimeters. Correspondingly, in such embodiments, the furthest depth the distal reaming tip 404 may extend anteriorly within the patient is 20 millimeters beyond the initial depth. Other ranges are within the scope hereof, such as 0 to 10 mm, 0 to 15 mm, or 0 to 25 mm.

With specific reference to FIG. 4C, various internal features of the depth control mechanism may be seen. As shown, knob 422 may extend within the housing 410 and be coupled to the circumference of the elongated rod 402. This connection may be facilitated by a threaded sleeve 432 that receives a proximal end 434 of elongated rod 402 therein. Pin 428 extends through outer sleeve 432 and elongated rod 402 within outer sleeve 432 such that pin 428 moves with movement of elongated rod 402. Outer sleeve 432 threadedly engages, via external threading 436 with corresponding internal threads 438 disposed within knob 422. When the knob 422 is rotated, the threaded engagement between threading 436, 438 causes longitudinal movement of rod 402 along a longitudinal axis 440 of the bone reamer instrument 400.

Further, the pin 428, via connection to rod 402 and being received within slot 427, causes rotation of rod 402 when housing 410 is rotated as pin 428 is carried with rotation of housing 410, thereby enabling the surgeon to effectuate the reaming action of distal reaming tip 404. The separation of the rotation of the elongated rod 402 for reaming bone and the rotation of the knob 422 for adjusting the longitudinal position of distal reaming tip 404 may provide safety advantages by preventing accidental penetration of the ligamentum flavum. The separation is achieved because knob 422 rotates independently from housing 410.

The external threading 436 and internal threading 438 may engage to move the elongated rod 402 distally along the longitudinal axis 440 to the point at which proximal end 434 contacts a proximal end of the knob 422. This location corresponds with the furthest anterior extension of the distal reaming tip 404 as further anterior extension is limited by the presence of knob 422. Likewise, the external threading 436 and internal threading 438 may engage to return the proximal end 434 proximally along the longitudinal axis 440 to the point at which it contacts the proximal end 408. Such location corresponds with the initial depth of the bone reamer instrument 400. As such, the integrated depth control may be configured to produce a reciprocal motion of the outer sleeve 432 toward the central passage 312 of the access portal 302, counteracting the possibility of advancing the bone reamer instrument 400 too far anteriorly, which could lead to piercing the dural sac, the spinal cord, or surrounding nerves of the vertebrae, and causing harm to the patient.

Additionally, knob 422 may be spring-loaded by an internal spring 430 to induce tactile feedback felt by the surgeon incrementally as the knob 422 is rotated. In some embodiments, the internal spring 430 may induce tactile feedback every 2.5 millimeters that the distal reaming tip 404 is anteriorly extended from the initial depth or posteriorly retracted back towards the initial depth. In some embodiments, the spring may be designed to induce tactile feedback at various other increments (e.g., at 0.5-millimeter increments, 1-millimeter increments, 1.5-millimeter increments, 2-millimeter increments, 5-millimeter increments, etc.). The knob 422 may comprise grooves (not shown) that engage the internal spring 430 to induce this tactile feedback. The grooves may be disposed 180 degrees apart on the knob 422, or at other intervals. Rotation of knob 422 may force internal spring 430 to ride along a proximal surface of the knob, and when the knob 422 is rotated such that a groove aligns with the 430//, the 430// drops into the groove, which may provide tactile feedback to the surgeon.

Bone Removal Instrument

Included within the surgical kit 200 may be two excision instruments, a bone removal instrument 500 and a soft tissue removal instrument 600, which the surgeon may utilize for the removal of a bone, a tissue, or some combination of both to decompress the spine. These removal instruments 500, 600 may be used at the discretion of the surgeon based on the anatomy of the interlaminar region. Additional considerations for removal instrument 500, 600 selection may relate to structures hindering access to the hypertrophied ligamentum flavum 120'.

FIGS. 5A-5I depict the bone removal instrument 500 which may be inserted through the access instrument 300 for the excision of bone and/or tissue. Similar to the initial positioning of the bone reamer instrument 400, the bone removal instrument 500 may be advanced through the central passage 312 up to the point at which a distal edge 502 abuts the handle 316.

Figure 5A:
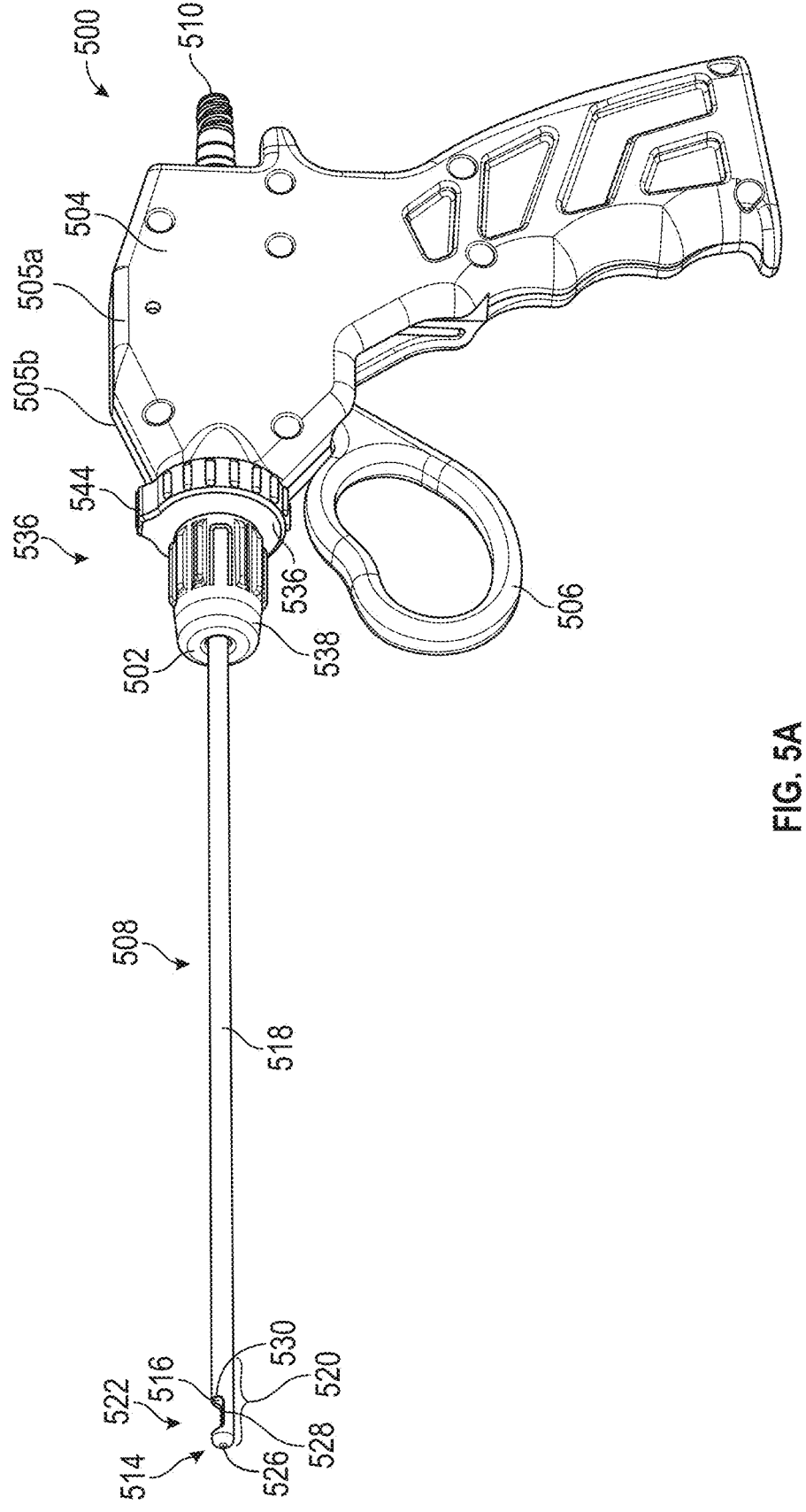
FIG. 5A depicts a perspective view of a bone removal instrument for some embodiments.
Figure 5B:
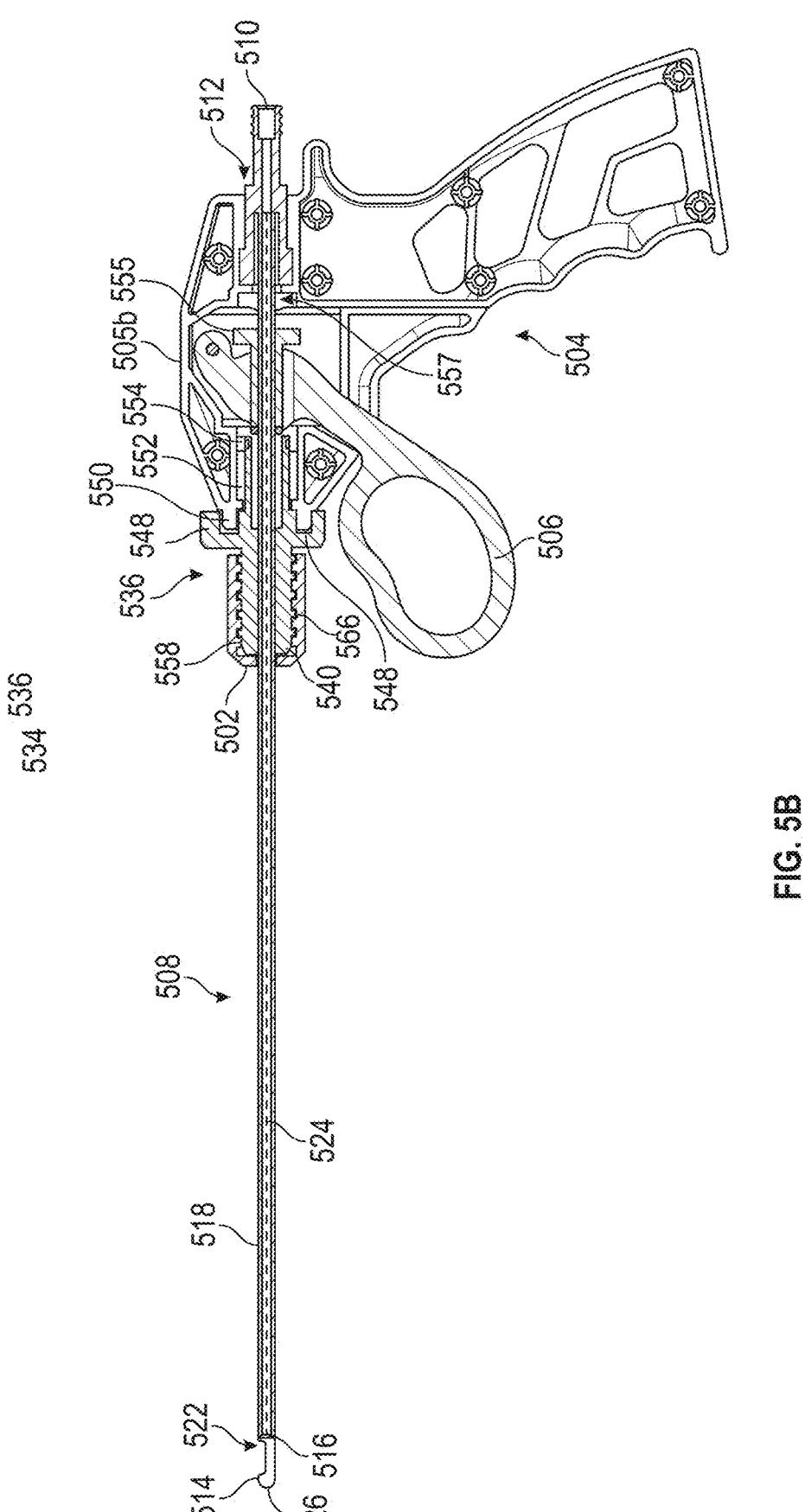
FIG. 5B depicts a cross-sectional view of the bone removal instrument for some embodiments.

FIGS. 5A and 5B provide a perspective view and a cross-sectional planar view, respectively, of the bone removal instrument 500 for some embodiments. In some embodiments, the bone removal instrument 500 may comprise a housing 504. The housing 504 may be coupled to both a trigger 506 and an elongated cutting assembly 508 configured to be actuated by the trigger 506. The housing 504 may comprise two halves 505a, 505b. A connection port 510 may extend from the housing 504 and be configured to couple to one or more external components for removal of bone/tissue from the instrument 500 as described in further detail below with respect to FIG. 5F.

The elongated cutting assembly 508 may comprise a proximal end 512 partially disposed within the housing 504 and a distal end 514 configured to be inserted into the patient. In some embodiments, the elongated cutting assembly 508 may comprise an inner shaft 516 and an outer tube 518. The outer tube 518 may extend the entire length of the elongated cutting assembly 508. The inner shaft 516 may be received within the outer tube 518 and extend within the elongated cutting assembly 508. In some embodiments, the inner shaft 516 is a solid shaft. It may be desirable to provide the inner shaft 516 as a solid shaft as the solid shaft may improve excision of bone and/or tissue as the solid shaft may be stronger than a similar hollow tube. However, in some embodiments, the inner shaft 516 is a tube, i.e., a hollow shaft.

The inner shaft 516 and the outer tube 518 may be used in conjunction to excise tissue and/or bone. The trigger 506 may be coupled to a circumference of the outer tube 518 within the housing 504. Namely, a bushing sleeve 555 may be coupled to the outer tube 518, and the trigger 506 may be received on an outer surface of the bushing sleeve 555. A distal end of the bushing sleeve may abut a proximal end of the trigger 506. As such, actuating the trigger 506 may force the bushing sleeve 555 proximally, which results in proximal longitudinal movement of the outer tube 518 due to the connection between the bushing sleeve 555 and the outer tube 518. When trigger 506 is pulled to its fullest extent, such that outer tube 518 is fully over inner shaft 516 at the distal end, bushing sleeve may be received within a recess 557 formed in housing 504. In some embodiments, the inner shaft 516 may be stationary, and movement of the outer tube 518 is relative to the inner shaft 516. Thus, engaging the trigger 506 toward the proximal end 512 may actuate the outer tube 518 to slide proximally toward the inner shaft 516 along a longitudinal axis 524 of the elongated cutting assembly 508. Slidably moving the outer tube 518 proximally may close or at least partially close the opening of the cutting cavity 522 and generate a cutting interface between the inner shaft 516 and outer tube 518 at the cutting region 520.

The elongated cutting assembly 508 may further comprise a cutting region 520 at the distal end 514 where tissue or bone excision occurs. When the trigger 506 is not engaged, the cutting region 520 may present a cutting cavity 522 in which bone and/or tissue is received and, when the trigger 506 is actuated to close the cutting cavity 522, the excised tissue and/or bone may be excised and received within the cavity 522. The cutting cavity 522 may be defined as an opening on the outer tube 518 and may be shaped to receive excised tissue and/or bone. It will be appreciated that any such geometry optimizing excised tissue reception may be used to define the opening of the cutting cavity 522 (e.g., a rectangular opening, a circular opening, an oval opening, a trapezoidal opening, etc.).

In some embodiments, the trigger 506 may be first engaged or held by the surgeon toward the distal end 514 as the bone removal instrument 500 is inserted into the access portal 302 (e.g., in the position illustrated in FIGS. 5A-B. In pushing the trigger 506 distally away from surgeon, the outer tube 518 may be extended to and held at a most distal position. Such a feature may ensure the cutting cavity 522 is not closed by movement of the outer tube 518 as bone removal instrument 500 is advanced into the patient. Depending on the patient anatomy, if cutting cavity 522 is forced close during insertion, it may be difficult to move outer tube 518 to open cutting cavity 522 while bone removal instrument 500 is in the patient. Thus, the forward positioning of the trigger 506 may advantageously be leveraged to ensure the cutting cavity 522 is configured in an open position to most effectively excise tissue after it has been advanced to the interlaminar space.

Figure 5C:
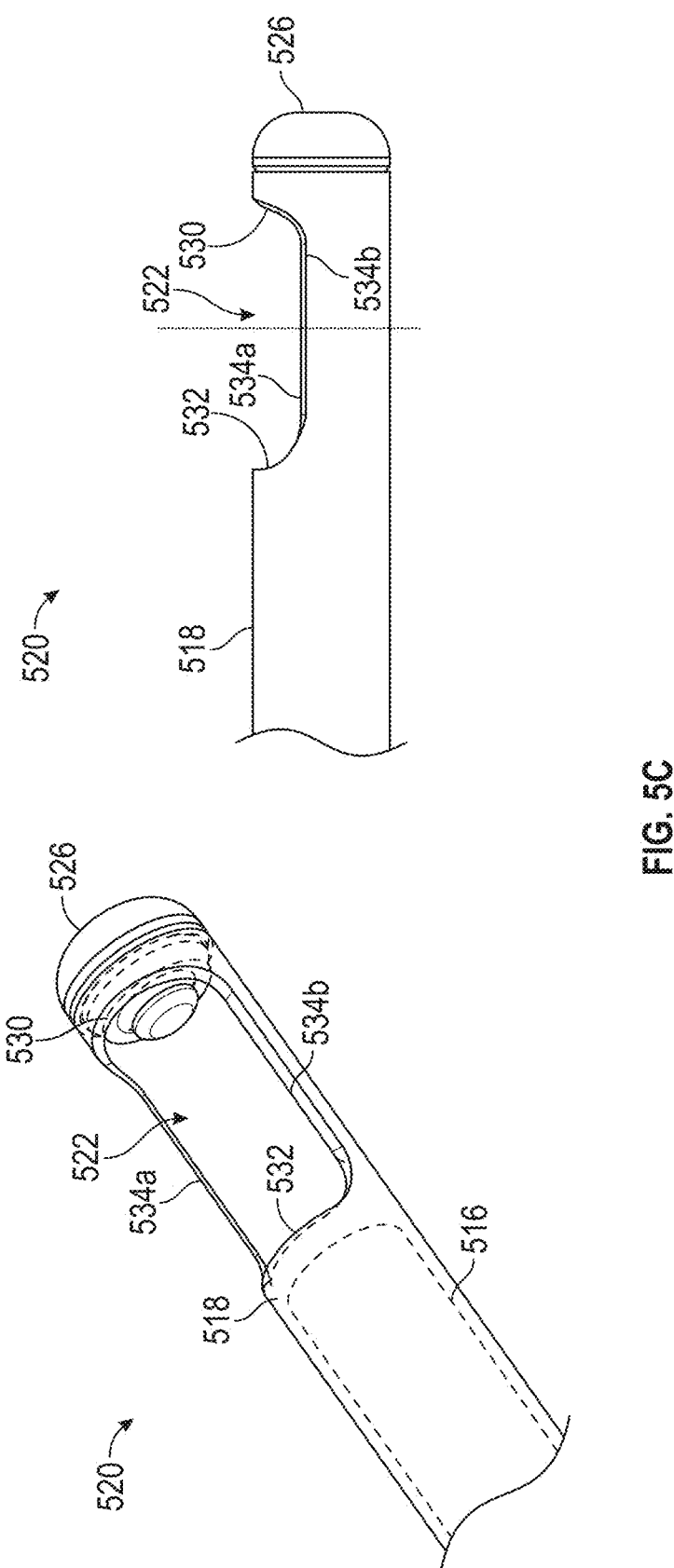
FIG. 5C depicts a close-up view of a cutting region of a bone removal instrument for some embodiments.

With specific reference to FIG. 5C, cutting region 520 may further comprise an arcuate tip 526. The arcuate tip 526 may be structured as a curved or otherwise blunt edge so as to mitigate damage to surrounding tissue and nerves. More specifically, the rounded end of the arcuate tip 526 may prevent anterior penetration into the dural sac during the insertion of the bone removal instrument 500 and throughout the decompression. In some embodiments, the arcuate tip 526 may comprise a distal groove 528 used to identify the location of the bone removal instrument in the patient (see FIG. 5E). The groove appears viewable under fluoroscopy while the structure around the distal groove 528 shows up as opaque. This feature may increase visibility of the instrument 500 throughout the procedure and provide an added safety factor by indicating to the surgeon where the distal-most point of bone removal instrument 500 is at within the patient, thereby minimizing the risk of piercing the ligamentum flavum and into the dural sac and spinal cord structure located anteriorly behind the ligamentum flavum.

Bone removal instrument 500 may further comprise an orientation control mechanism 536 and a depth control 538. The orientation control mechanism may be configured to rotate cutting region 520 to enable excision of tissue/bone at various orientations. Advantageously, this rotation may be done without requiring rotation for housing 504. Depth control 538, meanwhile, may provide another safety feature that may limit the anterior advancement of cutting region 520, and may further be adjustable so that the depth can be safely controlled by the surgeon during the decompression procedure. Both orientation control mechanism 536 and depth control 538 are discussed in detail below with respect to FIG. 5D.

FIG. 5C provides a close-up perspective and planar view of the cutting region 520 for some embodiments. The cutting cavity 522 of the cutting region 520 may be defined by a front edge 530 located near the distal end 514 and a back edge 532 proximal from the front edge 530. Side edges 534a, 534b extend between front edge 530 and back edge 532. The front edge 530 of the cutting cavity 522 may be angled relative to the edges 534a, 534b. As depicted in FIG. 5C, the front edge 530 may be angled forward toward the distal end 514. In some embodiments, this forward angle toward the distal end 514 may be a 10-to-20-degree angle between an axis perpendicular from edges 534a, 534b. In some embodiments, the angle may be some other angle between 0 and 45 degrees, or between 0 and 60 degrees. In some embodiments, the front edge 530 may be angled away from the distal end 514 in a negative angle relative to the vertical axis. In some embodiments, this negative angle, directed toward the proximal end 512, may be a 10-to-20-degree angle in which the front edge 530 is acute relative to the side edges 534a, 534b. In other embodiments, the negative angle may be some other angle between 0 and 45 degrees. Further still, the front and back edges 530, 532 may be perpendicular to the side edges 534a, 534b.

In some embodiments, the edges 530, 532, 534a, 534b of the cutting cavity 522 opening may be sharpened to aid in excising bone and/or tissue. As the cutting region 520 is rotated by an orientation control mechanism 536 (discussed further below), the sharpened cutting edges of the cutting cavity 522 may slice surrounding tissue, removing the tissue from the surrounding tissue without any actuation of the trigger 506 or engagement of a cutting interface at the cutting region 520 through movement of the outer tube 518. Further, in some embodiments, the arcuate tip 526 of the bone removal instrument 500 may additionally comprise teeth or other serrations along the edges 530, 532, 534a, 534b of the cutting cavity 522 for increased cutting capacity (as discussed further with reference to FIG. 5J).

Figure 5D:
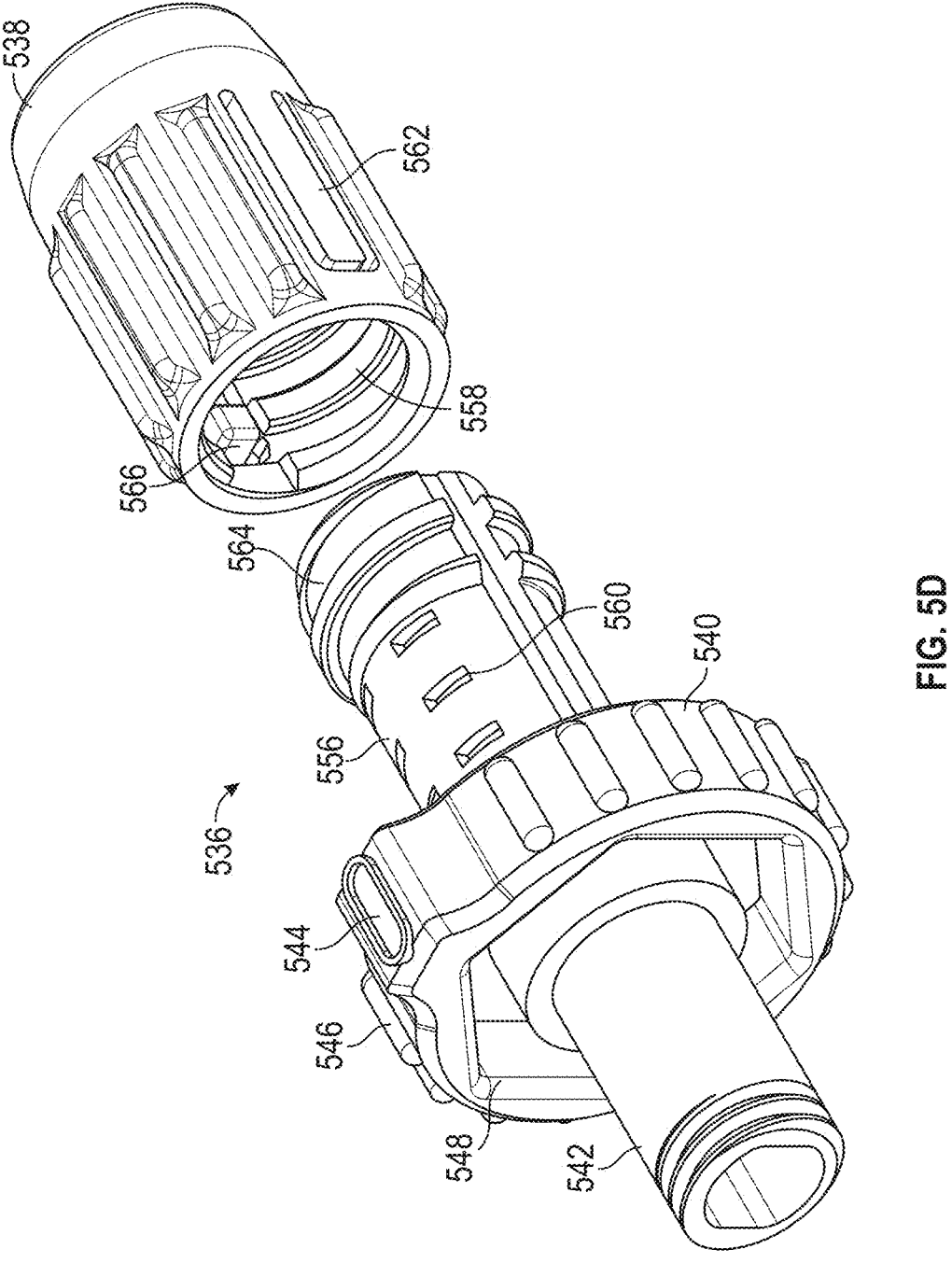
FIG. 5D depicts an exploded view of a depth control and orientation control assembly of the bone removal instrument for some embodiments.

FIG. 5D illustrates an exploded view of an orientation control mechanism 536 and depth control 538 of bone removal instrument 500. The orientation control mechanism 536 may comprise a knob 540 and a knob shaft 542. Knob shaft 542 may be integral with knob 540 or formed separately and coupled to knob 540. Knob shaft 542 may be coupled to the circumference of the elongated cutting assembly 508 and extend at least partially into the housing 504 (see FIG. 5B). Knob 540 connects to the exterior of knob shaft 542.

The coupling between knob 540 and knob shaft 542 may allow for the elongated cutting assembly 508 and, by extension, the cutting region 520 to rotate in conjunction with rotation of the knob 540. As such, rotating of the knob 540 to change the orientation of the cutting region 520 allows for a more ergonomic process in which the housing 504 need not be twisted. Such improvement may reduce surgeon fatigue and improve overall performance of the decompressive procedure by easing tissue and bone excision.

The knob 540 may further comprise an indicator 544 that corresponds with the angle at which the cutting region 520 is oriented for cutting. For example, in the illustrated position of indicator 544, the cutting cavity 522 would be facing upwards. Providing indicator 544 is advantageous because the orientation of cutting region 520 within the patient may be difficult (if not impossible) to see under fluoroscopy. Thus, providing indicator 544, which remains outside the patient and thus is viewable to the surgeon, ensures the surgeon always knows the orientation of cutting region 520.

Further, the knob 540 may comprise incremental grooves 546 that correspond to the default angle increments, which are locking points for the cutting region 520 orientation as the knob 540 is rotated. In some embodiments, the default angle increments may correspond with eight 45-degree angle increments around 360 degrees of potential rotation. In some embodiments, the angle increments may be an angle of any degree. For instance, the angle increments may be four 90-degree angle increments, or sixteen 22.5-degree angle increments. In some embodiments, the orientation of the cutting region 520 may be limited to only the incremental angles. In some embodiments, the rotation of knob 540 is not incremental, i.e., the rotation is continuous or stepless. At each increment of rotation, the orientation control mechanism 536 may induce tactile feedback felt by the surgeon as the knob 540 is rotated between various default angles. Such tactile feedback may be generated by an internal spring (not shown) within the housing 504 and adjacent to the knob 540.

With reference to FIGS. 5A-5B and 5D, it can be seen that knob 540 may be formed with a mating feature 548, which may have a hexagonal geometry, or other geometries, such as square, pentagonal, octagonal, or the like. The mating feature 548 may receive a corresponding boss 550 on the housing 504. The mating feature 548 and the boss 550 are formed with the same geometry to mate together. The knob 540 may be spring biased in a proximal direction to mate with the boss 550. A spring (not shown) may be disposed in a cavity 552 and captured by a bushing 554 having internal threads (not shown). Thus, to adjust the angle of cutting region 520 via orientation control mechanism 536, the surgeon may pull knob 540 distally to disengage mating feature 548 from boss 550 and then rotate knob 540 to achieve the desired orientation of cutting region 520. When the knob 540 is rotated to the desired position, the surgeon can release the knob 540, and the spring may bias the knob proximally to reengage with the boss 550.

In some embodiments, the internal spring may be captured by a threaded bushing (not shown) and may reciprocally push against a cavity wall within the housing 504. Such motion may drive the knob 540 toward the housing with an interacting male boss (not shown) and female mating feature (not shown) such that the spring may interact with the knob 540 when engaged. In some embodiments the male boss and female mating features may be a hexagonal shape; however, it will be appreciated that such features may be any number of two-dimensional geometries so long as they are of the same geometry for interaction purposes (e.g., a square, a rectangle, a circle, a heptagon, an octagon, etc.).

Knob shaft 542 may further comprise a depth gauge portion 556 extending distally from knob 540. Depth control 538 may be coupled to depth gauge portion 556 and adjustable along a length thereof to control a depth of cutting region 520 within the patient. Accordingly, the depth gauge portion 556 may comprise protrusions 558 extending longitudinally along a length thereof, depth indicators 560, and recesses 564. Depth control 538 may be adjustable 15 mm, as shown, or other lengths. Out of the surgical kit 200, bone removal instrument 500 may be configured with depth control 538 positioned at the distal most end (e.g., at 0 mm). Accordingly, the surgeon can move the depth control 538 proximally to extend the cutting region 520 anteriorly out of access portal 302.

To adjust depth control 538 along depth gauge portion 556, depth control 538 may comprise depressible tabs 562 and protrusions 558 that mate with recesses 564. The tabs 562 may comprise inward-facing protrusions 566 to secure depth control 538 to protrusions 558 (see FIG. 5D). When tabs 562 are depressed, the depth control 538 is disengaged from depth gauge portion 556 such that depth control 538 can be moved longitudinally along depth gauge portion 556 to extend cutting region 520 further out of access portal 302. Thus, the depth may be further adjusted anteriorly from this initial depth up to the largest measurement on the depth indicators 560 (e.g., 15 millimeters).

As mentioned, the depth indicators 560 indicate the depth that the bone removal instrument 500 is currently extended from the initial depth it is inserted at. In some embodiments, the depth indicators 560 may range from 0 millimeters to 15 millimeters and may include four marked increments at every 5 millimeters; however, it will be understood that the depth indicators 560 may comprise any other range. The depth indicators 560 may have the greatest measurement within the range, in this example the 15-millimeter measurement, at a proximal end of the depth gauge portion 556. The zero-measurement mark, indicating no adjustment to the depth of the instrument 500, may be the most distal mark along the depth gauge portion 556. As mentioned, this may be the starting position of depth control 538, and the surgeon may move depth control 538 proximally as desired to increase the depth of cutting region 520, such that the proximal-most position of depth control 538 represents a 15 mm distal extension of cutting region 520.

Figures 5E, 5F:
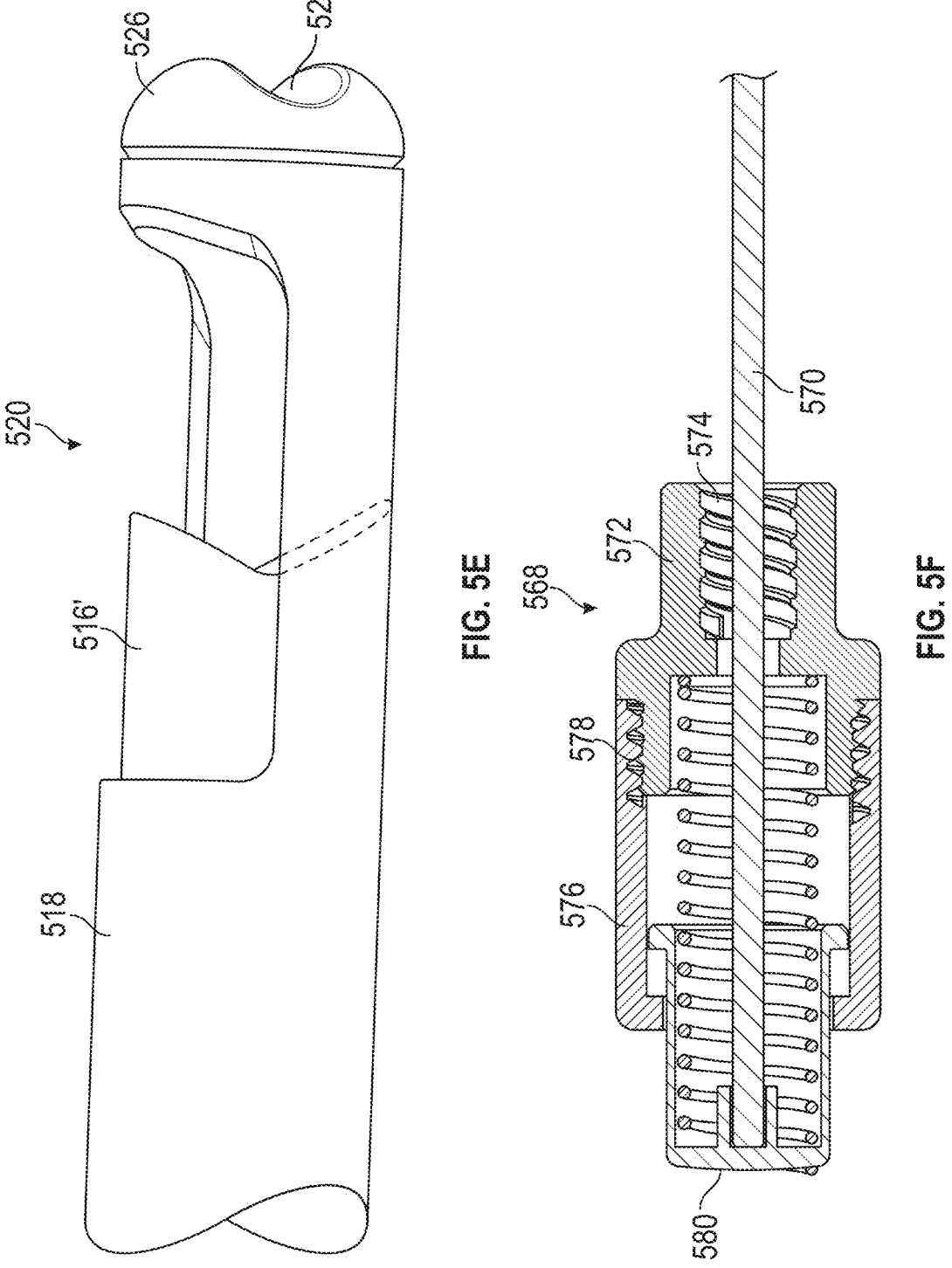
FIG. 5E depicts a close-up view of another cutting region of a bone removal instrument for some embodiments.
FIG. 5F depicts a cross-sectional view of a push rod assembly of the bone removal instrument for some embodiments.

Turning now to FIG. 5E, an embodiment of the cutting region 520 with inner shaft 516' formed with a "duck bill" geometry is illustrated for some embodiments. As compared to the circular cross-section of inner shaft 516 depicted in FIG. 5C, a duck bill geometry may be configured such that the upper and lower portions of the inner shaft 516' may extend more distally and may be oriented as forward, distally-extending angles relative to a vertical middle point of the inner shaft 516'. In some embodiments, the forward angles of the upper and lower portions may be the same angle. In some embodiments, the forward angles may differ such that one angle is greater than the other.

The angled configuration of the duck bill geometry may be utilized for expanded cutting capacity of the bone removal instrument 500. For example, the duck bill configured inner shaft 516' may be particularly useful in patients with spinal structures preventing direct access to the target area. For instance, the upper and lower forward angled portions may be especially advantageous in disengaging the cutting region 520 from a bony structure preventing excision of the hypertrophied ligamentum flavum. As previously discussed, the inner shaft 516' may be fixed without the capacity for rotation within the elongated cutting assembly 508. As the upper and lower forward angles may be appropriate for excision when fully aligned with the orientation of the cutting region 520, the angular orientation of the cutting region 520 may be restricted to a fully upward orientation and a fully downward orientation (i.e., the 0 degree and 180-degree orientation, respectively) for sufficient use of the duck bill geometry. The fully upward orientation of the cutting region 520 may allow for use of the upper forward angle in excision. Similarly, the downward orientation may allow the surgeon to utilize the lower forward-facing angle for cutting and disengaging purposes.

FIG. 5E further depicts the previously described distal groove 528 at the arcuate tip 526 for instrument identification of the duck bill cutting region 520 embodiment under imaging such as fluoroscopy.

Referring back to FIGS. 5A and 5B, the bone removal instrument 500 may further comprise a connection port 510 extending from the housing 504 at the proximal end of the instrument 500. In some embodiments, this connection port 510 may be a suction port specifically configured for removal of excised tissue and/or bone from the elongated cutting assembly 508 at the cutting region 520 via a vacuum attachment (not shown). The connection port 510 may be configured for removal of the excised tissue and/or bone from the elongated cutting assembly 508 using a vacuum to pull the excised tissue and/or bone toward the proximal end 512. Advantageously, use of connection port 510 allows for the removal of excised tissue and/or bone without necessitating the removal of the bone removal instrument 500 from the access portal 302. In some embodiments, the connection port 510 may be a Luer port configured to couple to a vacuum for suctioning the excised tissue and/or bone from the elongated cutting assembly 508. The Luer port may be a slip Luer configured such that attachments may be secured by inserting a male component into a female receptive piece at the connection port. In some embodiments, the connection port 510 is a Luer lock with a threaded or twisting connection for coupling to a vacuum. It is further contemplated that syringes and the like may be coupled to connection port 510 (e.g., using a corresponding Luer connection) to deliver fluids into the patient via connection port 510.

Looking now at FIG. 5F, a proximal assembly 568 for coupling to connection port 510 is illustrated for some embodiments. Proximal assembly 568 may be coupled to connection port 510 for removal of the excised tissue and/or bone from the elongated cutting assembly 508 and may present an alternative to removal of bone/tissue with a vacuum.

In some embodiments, proximal assembly 568 comprises a plunger rod 570 configured to be inserted into the inner shaft 516. The plunger rod 570 may be a solid rod and sized to extend from the proximal assembly 568 to the cutting region 520 at the distal end 514 of the excision instrument 500. The proximal assembly 568 may further comprise a first housing portion 572 with inner threads 574. The inner threads 574 may be used to threadedly secure the proximal assembly 568 to the housing 504 of the excision instrument 500 via the corresponding threads on connection port 510. The proximal assembly 568 may further comprise a second housing portion 576 that threadedly couples to housing portion 572 at a threaded interface 578 via internal threads on second housing portion 576 and external threads on first housing portion 572.

Second housing portion 576 may comprise an opening at a proximal end for receiving a spring-loaded button 580 therein. As shown, spring-loaded button 580 is coupled to the plunger rod 570. The spring-loaded button 580 may be actuated (depressed) to move the plunger rod 570 distally along the longitudinal axis 524 of bone removal instrument 500, pushing the excised tissue and/or bone from the elongated cutting assembly 508 out through the cutting cavity 522. Removal of tissue/bone using proximal assembly 568 may be done with the bone removal instrument 500 removed from the patient. The plunger rod 570 may have a diameter that is nearly the same as the inner diameter of the inner shaft 516 with only enough clearance such that movement of the plunger rod 570 along the longitudinal axis 524 is not hindered, e.g., the plunger rod 570 may form a close fit with the cannulated inner shaft. Providing rod 570 and inner shaft 516 with substantially the same outer diameter and inner diameter, respectively, may ensure ejection of the maximum amount of excised tissue and/or bone without permitting any bone and/or tissue to slip around the plunger rod 570 and remain in the elongated cutting assembly 508.

Figure 5G:
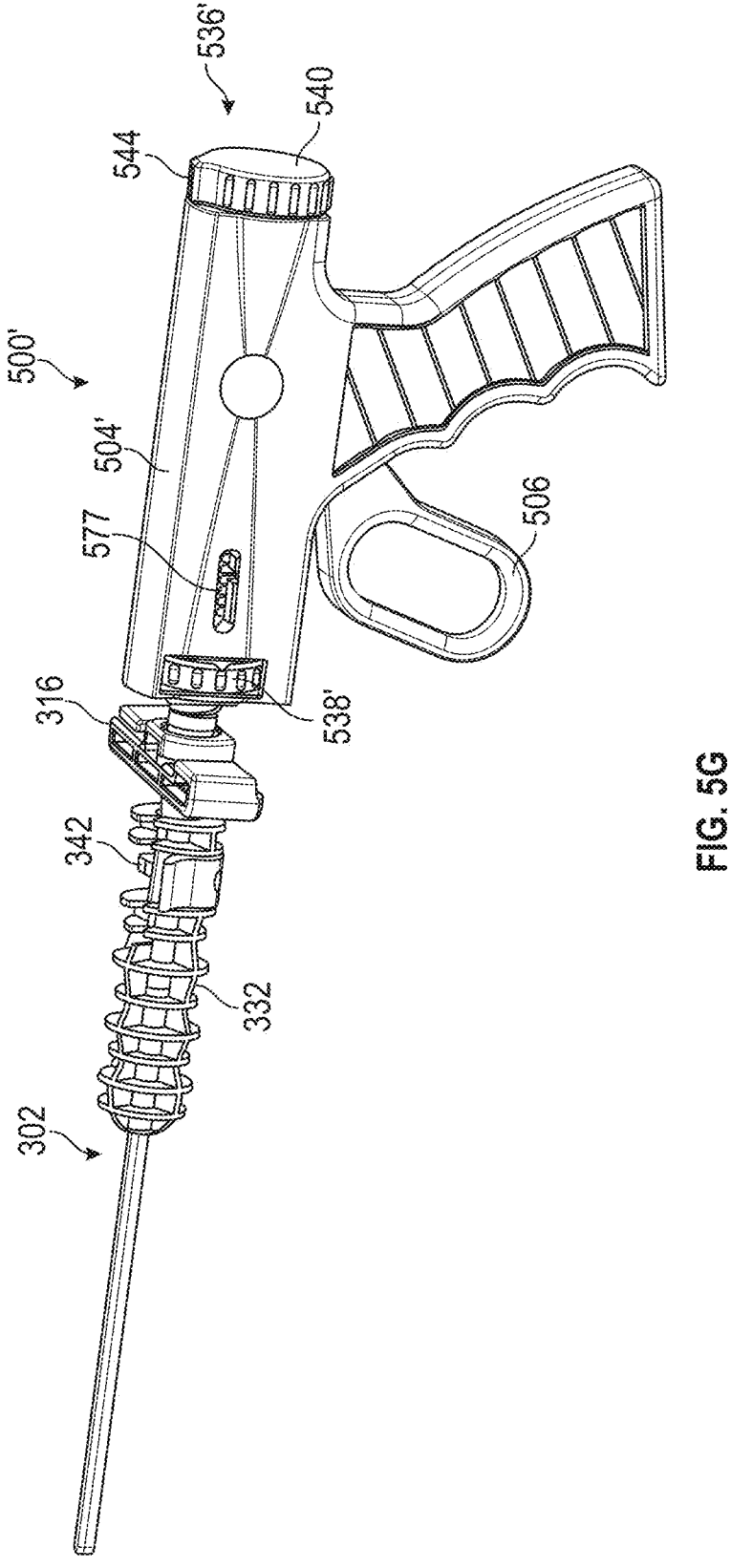
FIG. 5G depicts a perspective view of the bone removal instrument inserted through the access portal for some embodiments.

FIG. 5G illustrates the insertion of a bone removal instrument 500' through the access portal 302 of access instrument 300 with a backstop 332 coupled to the shaft 310 via the engaged cam lock 342. In this embodiment, the housing 504' may house a depth control 538', which may be a knob that extends through a window along the housing 504'. In some embodiments, this depth control 538' may be substantially similar to the depth control mechanism discussed with respect to access instrument 300. In some embodiments, depth control 538' may be substantially similar to the integrated depth control mechanism described with respect to the bone reamer instrument 400 and utilized to adjust the depth of the distal reaming tip 404 within the patient. For instance, the knob may tighten along the elongated cutting assembly via threading (not shown) as the bone removal instrument 500' is advanced beyond an initial insertion depth. Such tightening may occur when knob depth control 538' is rotated in a manner similar to the movement of elongated rod 402 described above. A window 577 may be formed in housing 504' such that a surgeon can view an indication of the position of the depth control 538' similar to the ruler described above. Additionally, the bone removal instrument 500' may comprise an orientation control mechanism 536' mechanism which may be located at the proximal end 512 of the instrument 500'. The orientation control mechanism 536' may be substantially similar to orientation control mechanism 536 on bone removal instrument 500.

As discussed above and seen in FIG. 5G, the bone removal instrument 500' is configured to be inserted through access portal 302 and abut the handle 316 of access instrument 300. The backstop 332 may be adjusted along shaft 310 to a desired position, where the distal most end may abut the patient's back (not shown). Each of the bone reamers, bone removal, and soft tissue instruments described herein may be similarly inserted into access portal 302 as depicted in FIG. 5G, and the depth controlled via backstop 332 and the depth control mechanisms on the respective instruments.

Figure 5H:
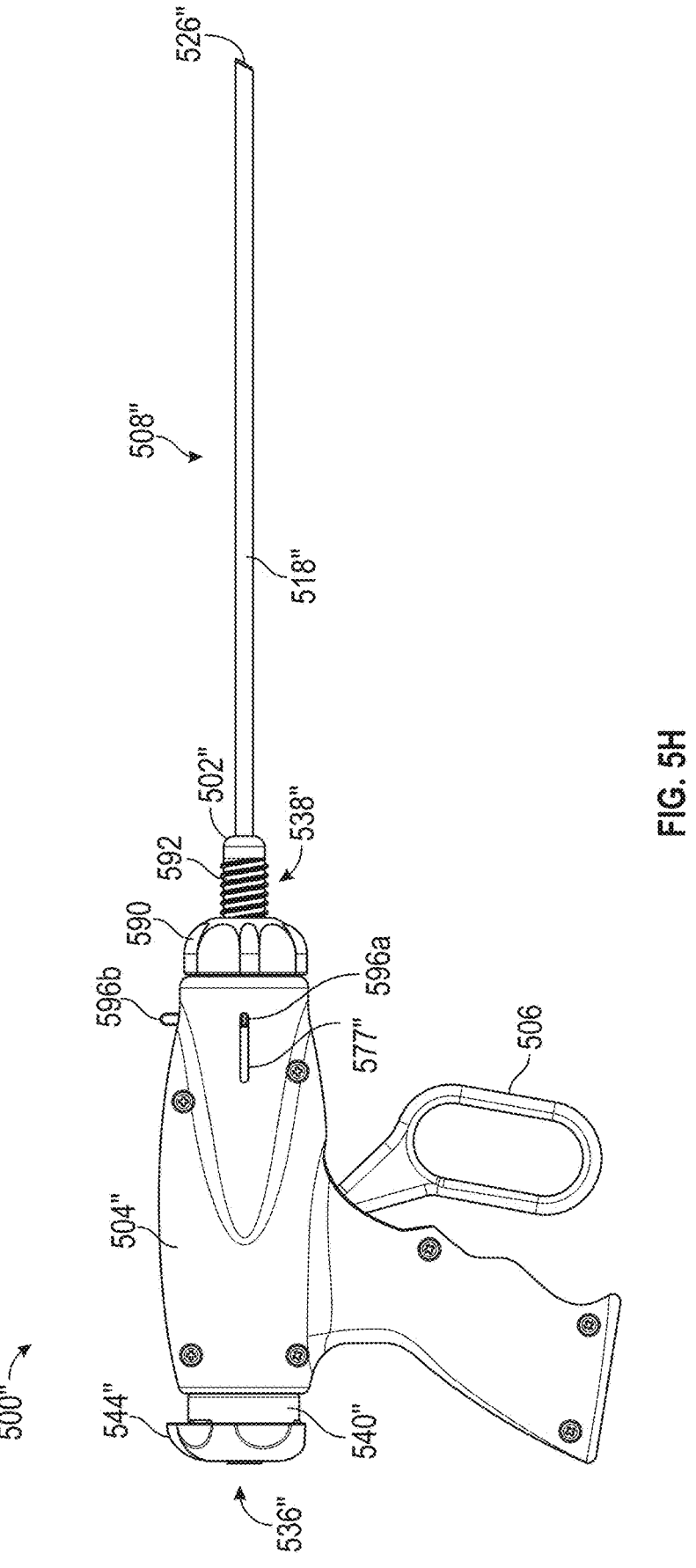
FIG. 5H depicts a side view of another bone removal instrument for some embodiments.
Figure 51:
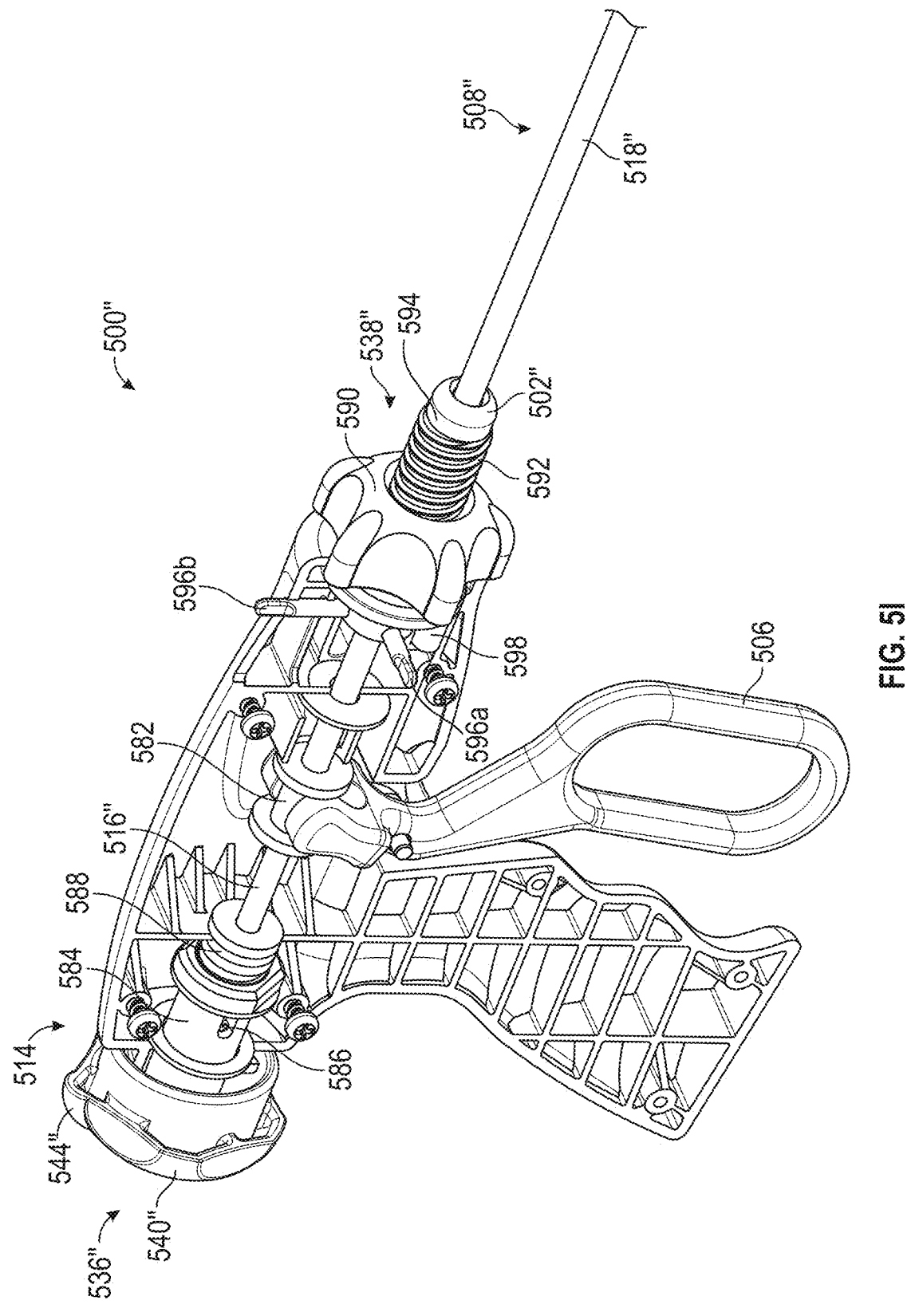

Turning now to FIGS. 5H and 5I, a bone removal instrument 500" is depicted for some embodiments. FIG. 5H is a planar view of bone removal instrument 500" for some embodiments, and FIG. 5I depicts bone removal instrument 500" with one half of the housing 504 removed so that various internal components are viewable. As with instruments 500, 500', bone removal instrument 500" may be configured to cut through bone and/or tissue to decompress the spine. Bone removal instrument 500" may include any of the features described with respect to bone removal instruments 500, 500' and vice versa. For example, as detailed below, bone removal instrument 500" comprises an orientation control mechanism on a proximal end thereof, and it is contemplated that either or both of instruments 500, 500' could likewise include an orientation control mechanism at this proximal location. In some embodiments, instrument 500" comprises a housing 504" that may be similar to the housings 504, 504' described above.

Bone removal instrument 500" may comprise an elongated cutting assembly 508" comprising an inner shaft 516" and an outer tube 518", and outer tube 518" may move longitudinally relative to inner shaft 516" to cut tissue and/or bone. As with instruments 500, 500', actuation of trigger 506 may cause the cutting action to occur. In some embodiments, inner shaft 516" comprises a cutting region substantially similar to the cutting region 620 described below with respect to FIGS. 6A-6E.

As shown, outer tube 518" may extend proximally from a tip 526" to an outer tube bushing 582 within the housing 504". In some embodiments, the outer tube 518" may terminate at the outer tube bushing 582 such that a portion of the inner shaft 516" not housed within the outer tube 518" may extend to a distal end 514 of the bone removal instrument 500" within the housing 504". The outer tube bushing 582 may receive the outer tube 518" through a central opening of bushing 582 such that an inner surface of bushing 582 contacts an outer surface of outer tube 518", e.g., the bushing 582 and outer tube 518" may have a friction fit.

In some embodiments, the outer tube bushing 582 may also be coupled to a portion of the trigger 506 internal to the housing 504' such that engagement of the trigger 506 may adjust the outer tube 518" by sliding busing 582 longitudinally. Specifically, a portion of the trigger 506 may be received within a recess of the bushing 582 such that movement of the trigger pulls the bushing 582 and, correspondingly, the outer tube 518" with the trigger. The outer tube 518" may slide longitudinally in accordance with engagement of the trigger 506 to enable bone cutting at the cutting region of the instrument 500".

As with bone removal instruments 500, 500', the elongated cutting assembly 508 may be rotated for improved cutting capacity via an orientation control mechanism 536". Here, bone removal instrument 500" may comprise an orientation control mechanism 536", which may be located at proximal-most end of bone removal instrument 500" and may be coupled to inner shaft 516" to rotate the shaft 516" to adjust the angle of the cutting element on the distal end of shaft 516". In some embodiments, the orientation control mechanism 536" may comprise a knob 540" having an indicator 544" at the distal end 514 of the instrument 500" corresponding to the angular orientation of the inner shaft 516". The knob 540" may further comprise a sleeve 584 coupled to the inner shaft 516" at an inner shaft bushing 588.

In some embodiments, the knob 540" comprises a slot that receives a pin 586, which is coupled to a proximal end of inner shaft 516". For example, the pin 586 may extend entirely through the proximal end, thus locking rotation of the pin 586, which itself may be rotated by the knob 540", to rotation of inner shaft 516". Thus, the surgeon may rotate knob 540" to cause a corresponding rotation of inner shaft 516". In some embodiments, the knob 540" may be spring-loaded, and the surgeon may pull knob 540" proximally to enable rotation of knob 540". Knob 540" may comprise an indicator 544" to indicate the orientation of the distal end of inner shaft 516".

Bone removal instrument 500" may also comprise a depth control 538" for the bone removal instrument 500". The depth control 538" may be substantially similar to the depth control mechanism described with respect to bone reamer instrument 400. Specifically, the depth control 538" may comprise internal threads (not shown) within depth control knob 590 that threadedly engage with external threads 592 on a sleeve 594. Sleeve 594 may couple to an outer surface of outer tube 518" to move outer tube 518" longitudinally via engagement of the threads 592 when depth control knob 590 is rotated in a manner similar to the movement of elongated rod 402 described above. Rotation of the depth control knob 590 may be utilized to modify the depth of the bone removal instrument 500" anteriorly beyond the initial depth of insertion through the access portal 302. The depth control knob 590 may comprise a distal edge 502" that may abut the handle 316 as the bone removal instrument 500" is inserted and advanced through the access portal 302. As in the case of the distal edge 502" of the bone removal instrument 500, the distal edge 502" of the bone removal instrument 500" may allow for an initial component of depth control prior to any anterior advancement at the depth control knob 590.

In some embodiments, the bone removal instrument 500" may further comprise a window 577" that receives a protrusion 596a therein. Window 577" may extend through both halves of housing 504", and a corresponding protrusion (not shown) may be disposed opposite the illustrated protrusion 596a through the window 577". A vertical protrusion 596b may extend out of a window/slot (not shown) in an upper surface of housing 504 The protrusions 596a, 596b may be coupled to sleeve 594 that receives the outer tube 518" to move the outer tube 518" longitudinally. In some embodiments, the protrusions 596a, 596b may indicate the anterior depth of the instrument 500" via a ruler on the housing 504.

Moreover, as shown in FIG. 5I, protrusion 596b may protrude from the housing 504 at a location between the protrusions 596a that are on the lateral or left/right sides of the housing 504. The surgeon can therefore obtain an indication of the depth of the cutting tip 526" via the protrusions 596a, 596b. By including multiple protrusions (e.g., one on each half of housing 504" and another on the top of housing 504"), the surgeon may be able to ascertain the depth of 526" regardless of the orientation of 500". For example, if the surgeon needs to rotate the instrument 500" during a cutting operation, the surgeon will have one of the lateral protrusions 596a visible.

Further, the depth control 538" may be spring biased via an internal spring 598, which may contact the depth control knob 590. The internal spring 598 may be engaged by rotation of the knob 540 to provide tactile feedback responsive to rotation of the inner shaft 516" as is the case for the bone reamer instrument 400. That is, internal spring 598 may function substantially similarly to internal spring 430.

Figure 5J:
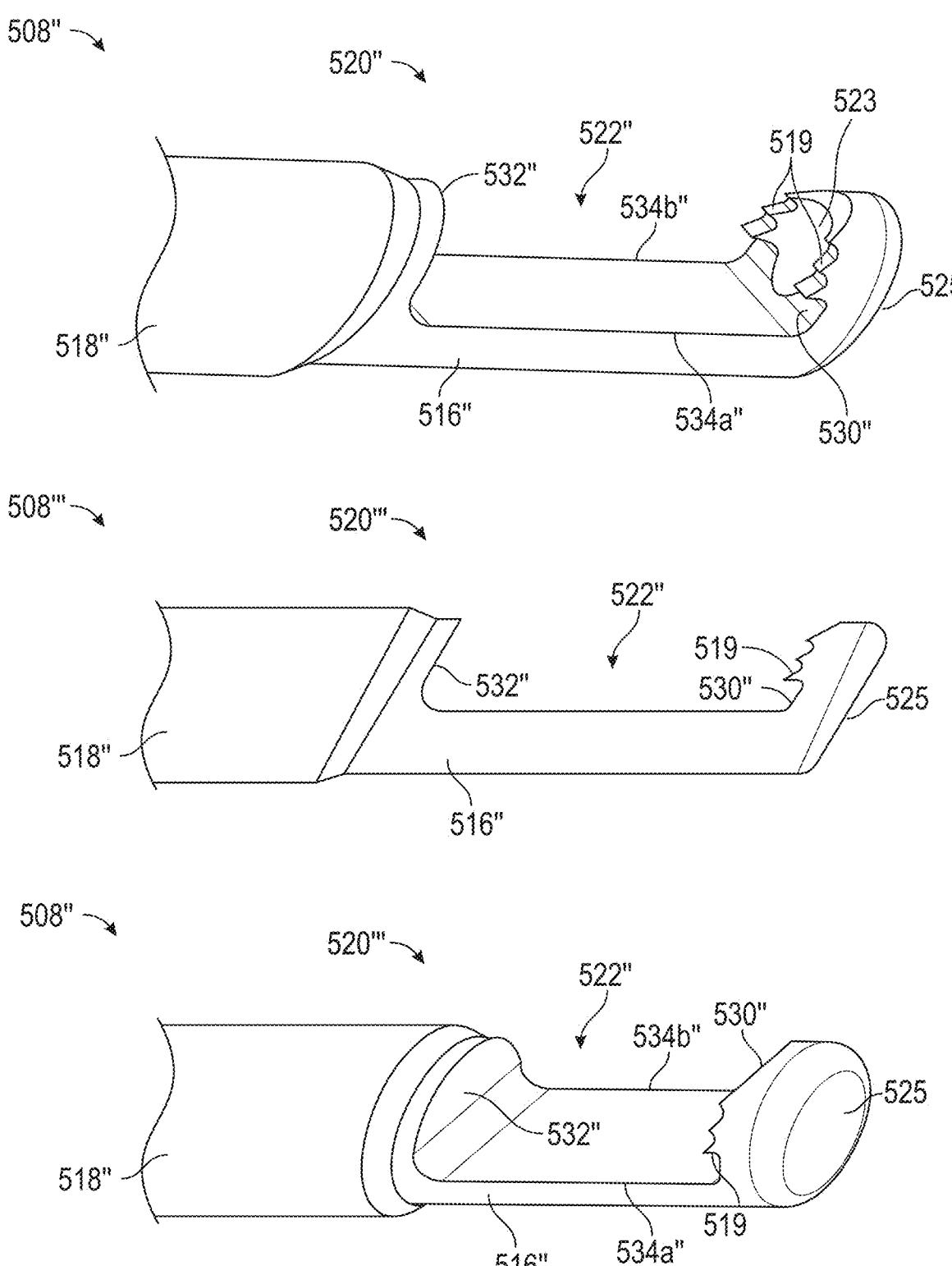
FIG. 5J depicts a close-up view of a cutting region of a bone removal instrument for some embodiments.

FIG. 5J depicts the elongated cutting assembly 508" for some embodiments, which may be used with any of the instruments 500, 500', 500" previously described. The elongated cutting assembly 508" may comprise an outer tube 518" substantially similar to the previously described outer tubes 518, 518". In some embodiments, the elongated cutting assembly 508" may comprise an inner shaft 516" corresponding to the inner shafts 516, 516' previously described. The inner shaft 516" may extend within the elongated cutting assembly 508" and be received within the outer tube 518". In some embodiments, the inner shaft 516" may slidingly engage with the outer tube 518" along a longitudinal axis such that the inner shaft 516" and the outer tube 518" may be used in conjunction to cut tissue and/or bone. Specifically, the outer tube 518" may be stationary in some embodiments, and actuation of a trigger 506 may enable the inner shaft 516" to slide proximally toward the stationary outer tube 518".

In some embodiments, the elongated cutting assembly 508" may comprise a cutting region 520" presenting a cutting cavity 522" at which excision may occur. The cutting region 520" may comprise a front edge 530", a back edge 532", and side edges 534a", 534b" formed as part of inner shaft 516", and the edges may be substantially similar to the respective edges 530, 532, 534a, 534b described with respect to FIGS. 5H and 5I. In some embodiments, the proximal edge 532" may be angled at an acute angle relative to side edge 534a" toward the distal edge 530" and may be chamfered or otherwise beveled (i.e., having a fillet) at the location along the cutting region 520". In some embodiments, the chamfered or beveled portion aids in retaining tissue in the cutting cavity 522".

In some embodiments, the cutting region 520" may further comprise teeth 519, which may be utilized to prevent slippage between the surrounding bone and/or tissue during excision efforts from the cutting region. That is, the teeth 519 may grab the tissue and/or bone and hold it until it is cut via the sliding action of the tube 518" and shaft 516" as previously described. In some embodiments, teeth 519 may extend from the front edge 530" toward the cutting cavity 522" to aid in gripping during longitudinal movement of the cutting region 520". It will be appreciated that, while teeth 519 may be located at the distal edge 530" to improve in tissue grip, teeth 519 may be located along any of the other cutting cavity 522" edges to achieve such grip improvement. For instance, teeth 519 may be spaced along the side edges 534a", 534b" in some embodiments. Teeth 519 may be located at any single edge 530", 532", 534a", 534b" along the cutting cavity 522" or any combination of edges thereof. A distalmost end 525 of the cutting assembly 508" may form an obtuse angle relative to the horizontal/relative to the edges 534a", 534b". Further, distal end 525 may be flat. Both the flat surface and the obtuse angle may prevent penetration of the cutting assembly 508" too far distally when in the interlaminar region.

In some embodiments, the teeth 519 may be a plurality of serrated or otherwise sharpened extensions. In some embodiments, there may be three teeth 519 as depicted in FIG. 5J; however, the number of extensions may not be less or greater than three (e.g., one tooth, two teeth, four teeth, and so forth). Additionally, in some embodiments, the teeth 519 may be oriented in various alternative spacing configurations rather than in a continuous linear configuration (i.e., along unique and offset vertical placements). Additionally, cutting assembly 508" may comprise a recess 523 configured to receive bone and/or tissue during excision. The recess 523 may be located between the teeth 519.

Soft Tissue Removal Instrument

Figure 6A:
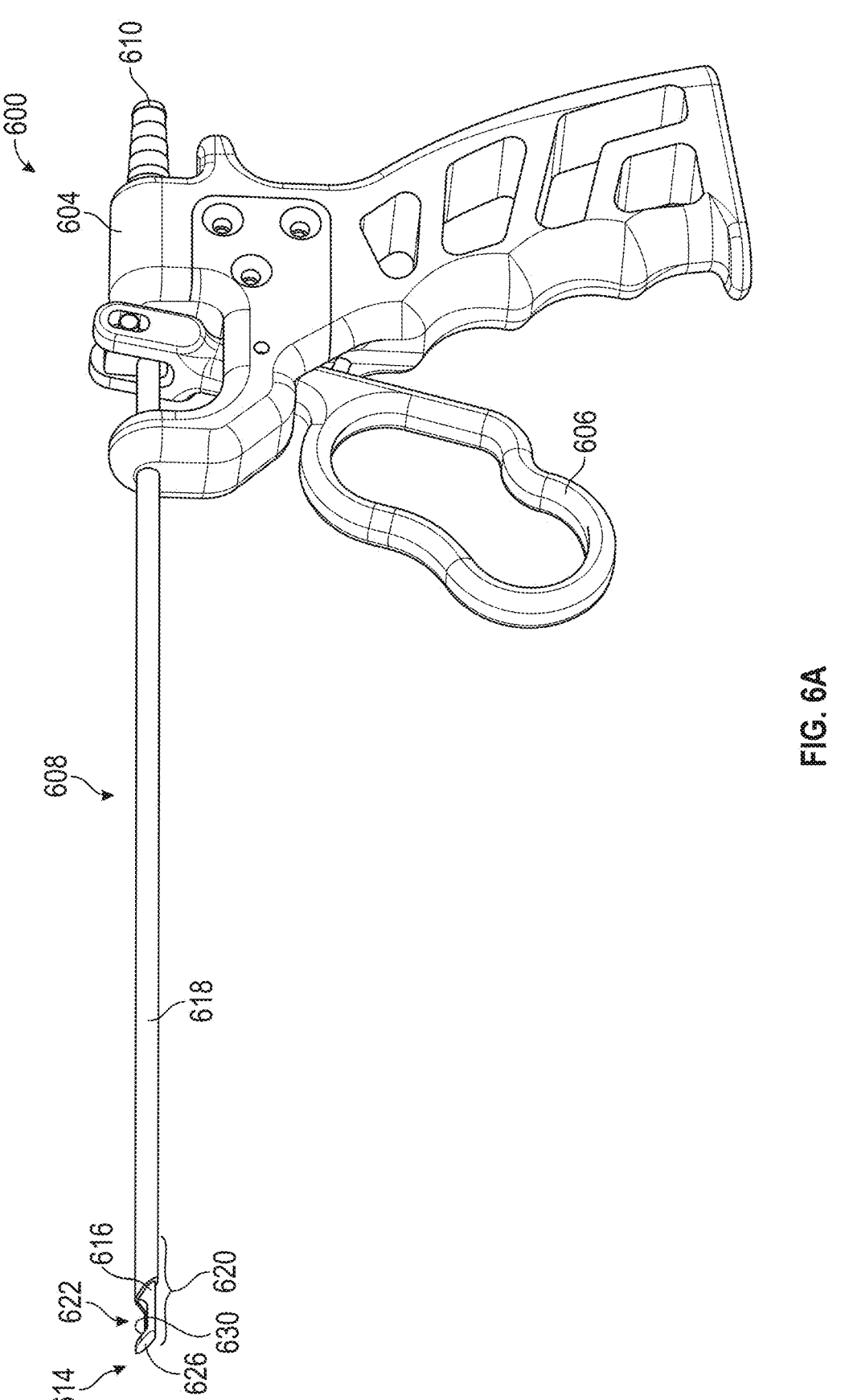
FIG. 6A depicts a perspective view of a soft tissue removal instrument for some embodiments.
Figure 6B:
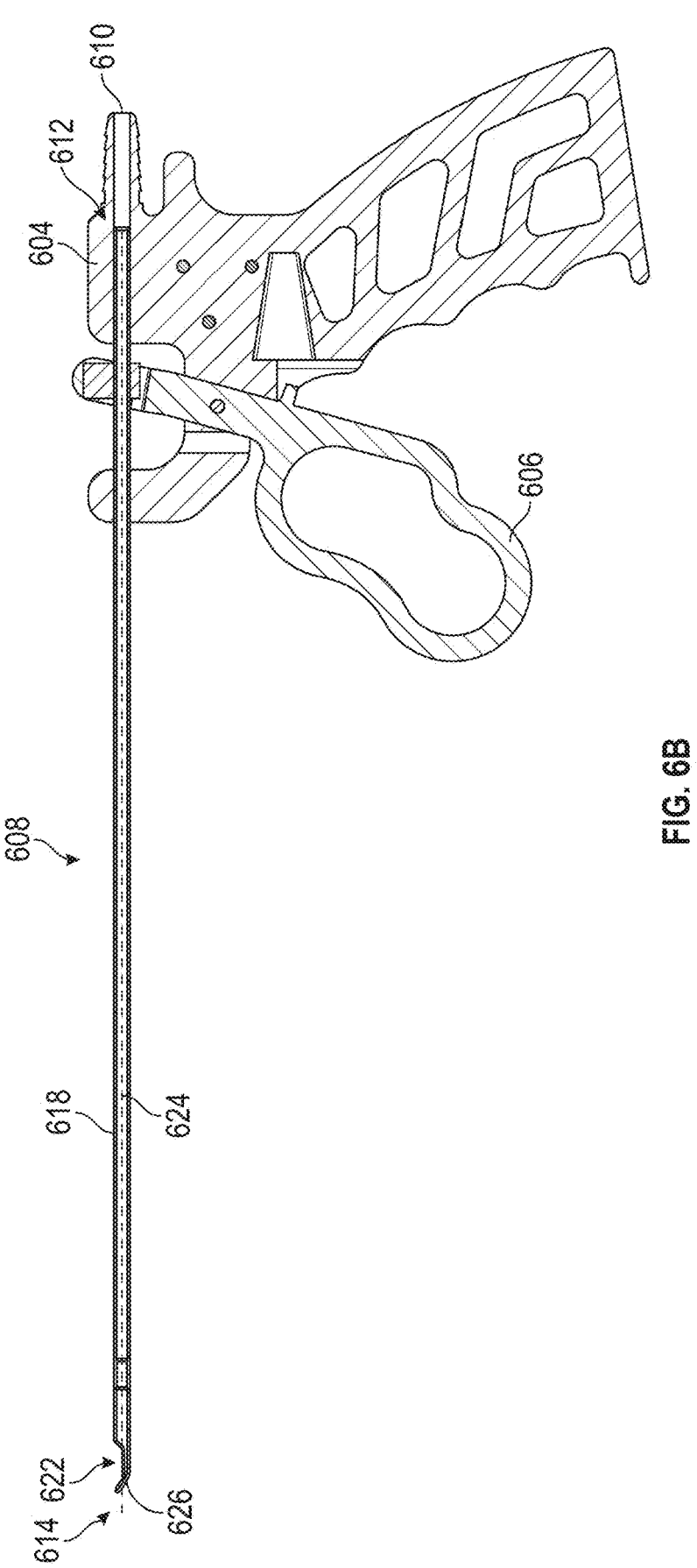
FIG. 6B depicts a cross-sectional view of the soft tissue removal instrument for some embodiments.

Turning now to FIGS. 6A-6D, the soft tissue removal instrument 600 is illustrated for some embodiments. As shown in FIGS. 6A and 6B, the soft tissue removal instrument 600 may be a rongeur-like instrument configured for excision of tissue, such as the hypertrophied ligamentum flavum 120'. Soft tissue removal instrument 600 may have a number of components substantially similar to those described with respect to bone removal instrument 500. These may include the housing 604, the trigger 606, the connection port 610, the proximal assembly 662, or any combination thereof. While not shown in the FIGS. 6A and 6B, it will be understood that the soft tissue removal instrument 600 may include an orientation control mechanism 536 as discussed with respect to bone removal instrument 500 to adjust the orientation of the cutting region 620.

Similar to bone removal instrument 500, the soft tissue removal instrument 600 may comprise an elongated cutting assembly 608 with a proximal end 612 at least partially enclosed within the housing 604 and a distal end 614 configured to be inserted into the patient. Further, like elongated cutting assembly 508, cutting assembly 608 may comprise a cannulated inner tube 616 received within a cannulated outer tube 618. In some embodiments, the inner tube 616 may also be stationary. As in the bone removal instrument 500, the outer tube 618 may slide along a longitudinal axis 624 of soft tissue removal instrument 600, while the inner tube 616 remains fixed to generate a cutting interface at the cutting region 620. Further, the soft tissue removal instrument 600 may comprise an arcuate tip 626 at the most distal end 614 to prevent damage to surrounding tissue and spinal structures during excision at a target area, e.g., to aid in preventing penetration of an anterior portion of the ligamentum flavum.

Figure 6C:
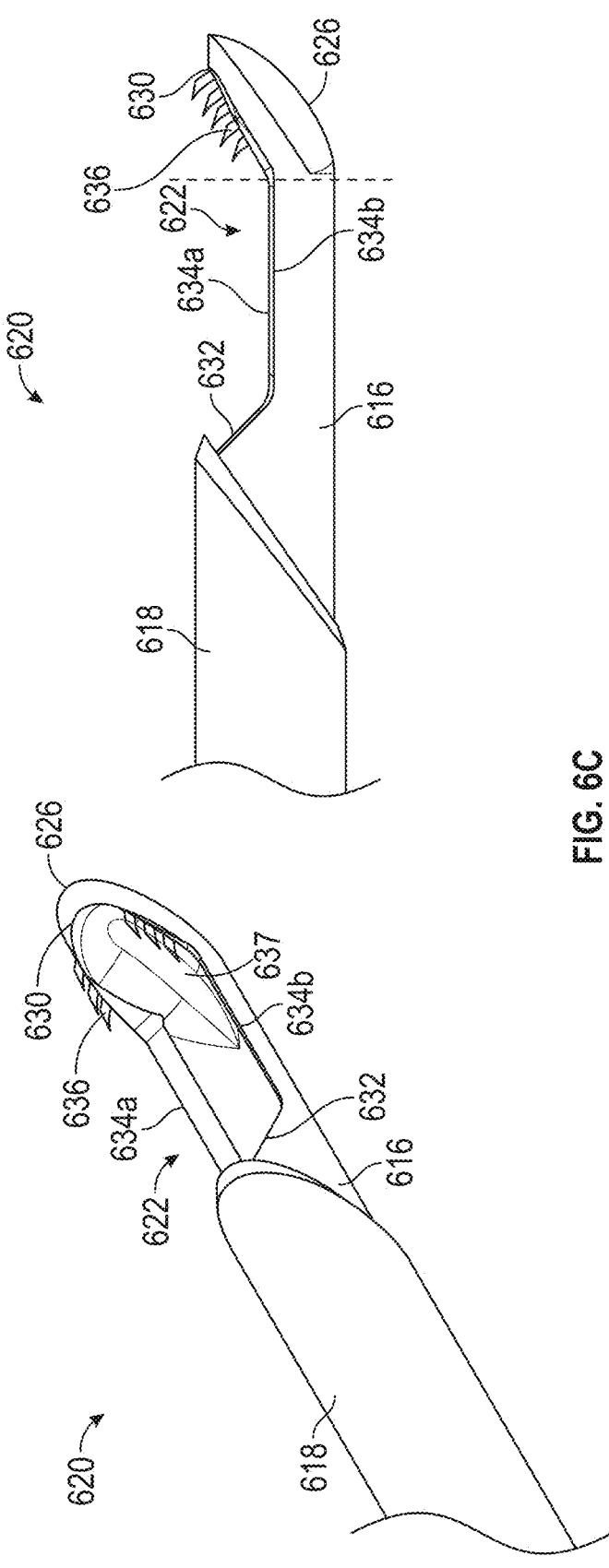
FIG. 6C depicts a close-up view of a cutting region of the soft tissue removal instrument for some embodiments.

As discussed, the soft tissue removal instrument 600 may be configured to excise soft tissue rather than both tissue and bone, and therefore, may comprise a cutting region 620 that differs from the cutting region 520 of bone removal instrument 500. However, it is contemplated that any of the cutting regions described herein may be used on the bone removal instrument and/or the soft tissue removal instrument FIG. 6C provides perspective and planar views of cutting region 620 for some embodiments. As shown, inner tube 616 extends out from a distal end of outer tube 618. Moreover, actuation of the trigger 606 may enable the outer tube 618 to slide distally along the longitudinal axis 624 toward the more distal inner tube 616 to at least partially close the cutting cavity 622. The soft tissue removal instrument 600 may be configured such that the outer front edge 630, back edge 632, and both side edges 634a, 634b are on the inner tube 616. In some embodiments, the front edge 630 may be oriented 20 or 30 degrees relative to the side edges 634a, 634b of the cutting cavity 622. In some other embodiments, the front edge may be any forward angle. Still further, the front edge 630 may be perpendicular to the side edges 634a, 634b. Any of edges 630, 632, 634a, 634b may be sharpened to aid in excising tissue.

In some embodiments, each of the edges 630, 632, 634a, 634b may be sharpened to form a continuous cutting edge around the cutting cavity 622, allowing a surgeon to manipulate the soft tissue excision instrument 600 to cut surrounding tissue in a sweeping motion (or other rotational motion) rather than just via longitudinal movement of the elongated cutting assembly 608. Further, the cutting region 620 may additionally comprise teeth 636 in some embodiments. The teeth 636 may be utilized to prevent slippage between the soft tissue excision instrument 600 and the surrounding tissue during excision. That is, the teeth 636 may grab the tissue and hold it until it is cut via the trigger is actuated to slide tube 618 relative to tube 616 to cut tissue as previously described. The teeth 636 may be substantially similar to the teeth 519 described above with reference to FIG. 5J. In some embodiments, the number of teeth is two, three, four, or more. In some embodiments, the cutting region comprises a cavity 637 for receiving the excised tissue, and teeth 636 are disposed on opposite sides of the cavity. Thus, in some embodiments, teeth are provided in pairs with each tooth of the pair being on a side of the cavity 637, and there may be one, two, three, or more pairs of teeth. It will be appreciated that teeth 636 may not be provided in pairs and that the number of teeth on one side of the cavity 637 may not match the number of teeth on the other side of the cavity. Further, the teeth 636 may or may not be aligned on either side of the cavity 637.

Figures 6D, 6E:
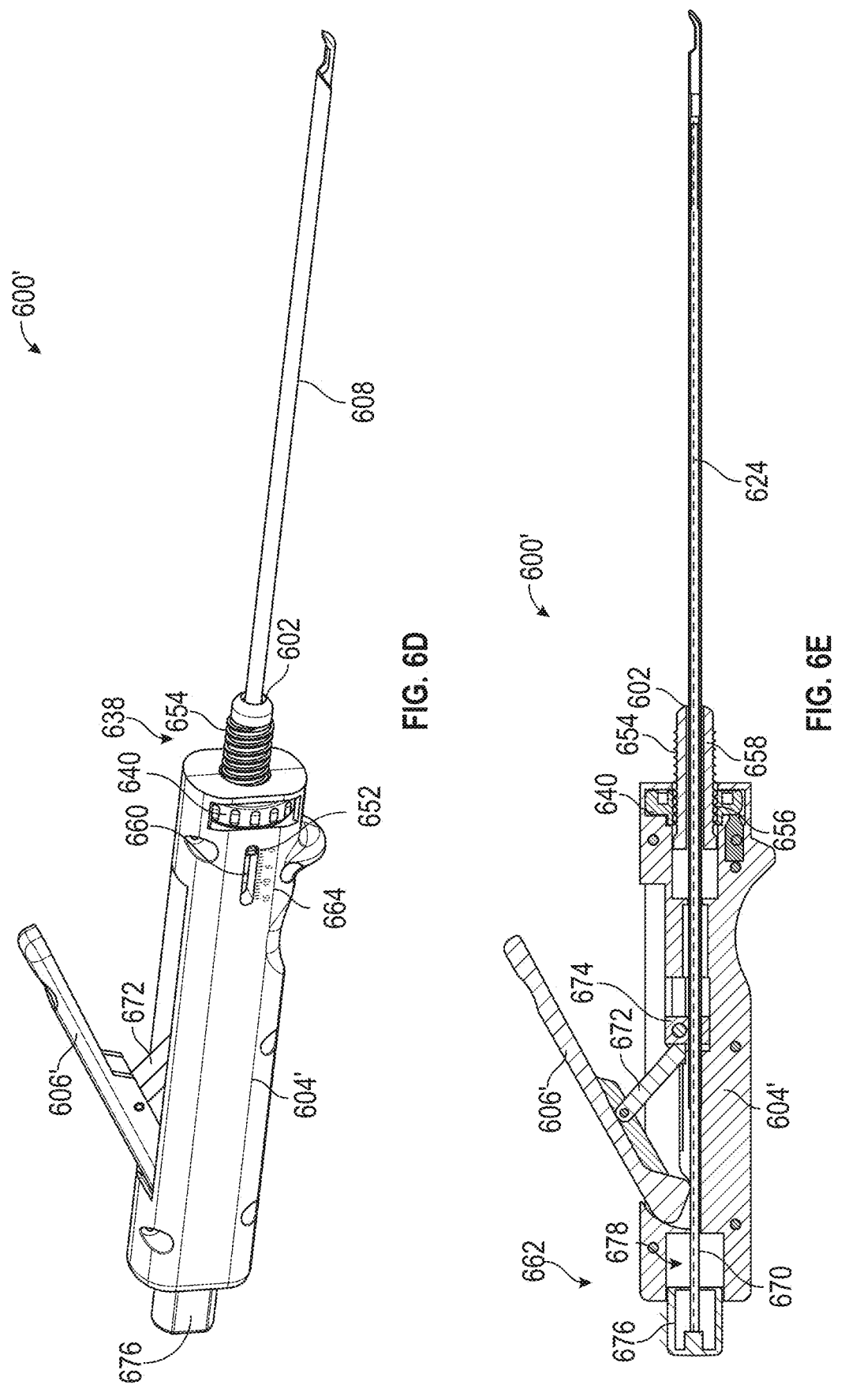
FIG. 6D depicts a perspective view of another soft tissue removal instrument for some embodiments.
FIG. 6E depicts a cross-sectional view of another soft tissue removal instrument for some embodiments.

FIGS. 6D and 6E depict an alternative embodiment of the soft tissue removal instrument 600' in which the housing

604' and trigger 606' may have a differing structure compared to housing 604 and trigger 606, which is referred to as a cigar-style handle. To cut tissue, the trigger 606' may be pushed inward (downwards in the view of FIGS. 6D-E) toward the housing 604' to engage a linkage 672. The linkage 672 may be coupled on one end to the trigger 606' and an opposing end to an attachment block 674. The attachment block 674 may couple to the exterior circumference of the outer tube 618 of the elongated cutting assembly 608, i.e., outer tube 618 passes through attachment block 674. Engagement of the trigger 606 may cause movement of the linkage 672 along a longitudinal axis 624 of the elongated cutting assembly 608 toward the distal end 614 via the corresponding movement of attachment block 674.

A depth control 638 for the soft tissue removal instrument 600 is also depicted at FIGS. 6D and 6E. This depth control 638 may be substantially similar to the depth control mechanism to the depth control mechanism described with respect to bone removal instruments 500', 500". In some embodiments, the depth control 638 may comprise internal threads 656 on knob 640 and external threads 654 on a sleeve 658. Sleeve 658 may receive outer tube 618 to move outer tube 618 longitudinally via engagement of the threads 654, 656 when knob 640 is rotated in a manner similar to the movement of elongated rod 402 described above. Rotation of the knob 640 may be utilized to modify the depth of the soft tissue removal instrument 600 anteriorly beyond the initial depth of insertion through the access portal 302. As described with respect to FIGS. 5H-5I, the knob 640 may similarly comprise a distal edge 602 that may abut the handle 316 as the soft tissue removal instrument 600 is inserted and advanced through the access portal 302. As in the case of the distal edge 502 of the bone removal instruments 500, 500", the distal edge 602 of the soft tissue removal instrument 600 may allow for an initial component of depth control prior to any anterior advancement at the knob 640.

In some embodiments, the soft tissue removal instrument 600 may further comprise a slot 660 that receives a protrusion 652 therein. A corresponding protrusion may be disposed opposite the illustrated protrusion 652. As with the depth control mechanism of access instrument 300, the protrusion 652 may be coupled to sleeve 658 that receives the outer tube 618 to move the outer tube 618 longitudinally. A ruler 664 may indicate the anterior depth of the instrument 600.

Further, soft tissue removal instrument 600 may comprise a proximal assembly 662 attached at the proximal end 612. Soft tissue removal instrument 600 may comprise a plunger rod 670 for excised tissue removal may be seen in both FIGS. 6D and 6E. Proximal assembly 662 may comprise plunger rod plunger rod 670 coupled to a button 676, which may be configured to be advanced distally into a cavity 678 to move plunger rod 670 distally to force tissue into cutting cavity 622. In some embodiments, the proximal assembly 662 may be attached in a similar manner as the proximal assembly 568 of the bone removal instrument 500 at a connection port 610.

The proximal assembly 662 may be operated to move the plunger rod 670 along the longitudinal axis 624 toward the distal end 614 to eject the excised tissue from the cutting region 620. In some embodiments, the button 676 may likewise be a spring-loaded button, which may be depressed by a surgeon into cavity 678 to initiate the movement of the plunger rod 670 along the longitudinal axis 624 toward the distal end 614 to eject the excised tissue from the cutting region 620. The spring (not shown) may then bias plunger rod 670 proximally into the illustrated position shown in FIG. 6E.

It will be appreciated that the instruments of the surgical kit 200 may be constructed of various materials. In some embodiments, at least one of the instruments 300, 400, 500, 500', 600, 600' is formed via an additive manufacturing process. In some embodiments, at least one of the instruments comprises RULON or PEEK. In some embodiments, the housings 504, 604, are overmolded. In some embodiments, the cutting assemblies 508, 608 are formed from a metal, such as steel, aluminum, titanium, or alloys thereof. In some embodiments, the entire instruments are formed from a metal, such as steel, aluminum, titanium, or alloys thereof. In some embodiments, any of the instruments may be formed from polyacrylamide or IXEF®. In some embodiments, the instruments are radiopaque or radiolucent, or at least a portion of the instruments (e.g., the portion inserted into the patient) are radiopaque or radiolucent. In some embodiments, any of the instruments are configured to be disposable, i.e., are single use instruments. In some embodiments, the instruments are configured to be reusable.

Surgical Methods

Figure 7:
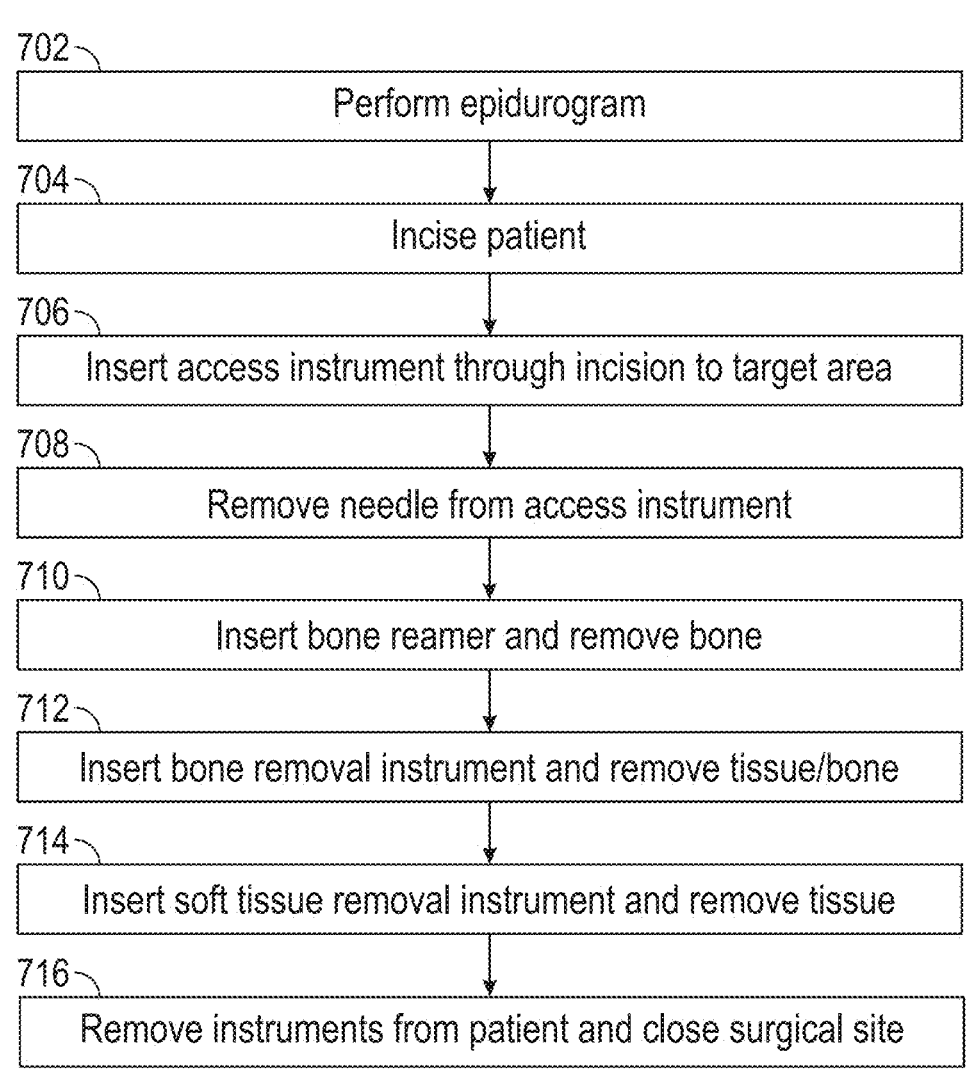
FIG. 7 depicts a method for a minimally invasive decompression procedure for some embodiments.

The previously described instruments may be used for the excision of hypertrophied ligamentum flavum 120' in the lumbar region, along with other surrounding tissue and bone as necessary to decompress a vertebra. Turning to FIG. 7, a method 700 is depicted, detailing the procedural steps of a percutaneous closed tissue excision procedure for some embodiments.

First, at step 702, the surgeon may perform an epidurogram on the patient prior to beginning the surgery. Performing an epidurogram may involve injecting a fluid such as a contrast medium (i.e., a contrast dye) into the epidural space of the spine to assess the structure of the epidural space. The epidurogram may further be leveraged to monitor the procedure under imaging such as, but not limited to, fluoroscopy. Other imaging modalities, such as endoscopic imaging, computed tomography (CT), magnetic resonance imaging (MRI), X-ray imaging, and ultrasound, are within the scope hereof.

Subsequently, at step 704, the surgeon may create an incision at a back surface of a patient positioned in a prone position. The incision creates a surgical site that may be made directly over the stenotic region of interest. In other procedures, the incision may be located along the back at an offset distance inferiorly and/or laterally relative to the stenotic region of interest. The incision may then be utilized to establish an initial point of insertion of the access instrument 300 during advancement to the stenotic region.

At step 706, an access instrument 300 may be inserted through the incision and advanced to the interlaminar space of the spine to access hypertrophied ligamentum flavum 120'. A removable portion 318 of the access instrument may create the path to the interlaminar space as described above. When at the desired location within the patient or when bone (e.g., lamina) prevents further advancement of access instrument 300 using needle 322, the removable portion 318 may be removed from the access instrument 300 at step 708 while the access portal 302 is retained within the patient. Retention of the access portal 302 within the patient may provide a percutaneous path extending beyond the back surface of the patient through which any of the other instruments included in the kit (i.e., the bone reamer instrument 400, the bone removal instrument 500, and the soft tissue removal instrument 600) may be inserted.

Following removal of the removable portion 318 of the access instrument 300, a bone reamer instrument 400 may be optionally inserted through the access portal 302 to remove bony structures preventing access to the ligamentum flavum at step 710. In such instances where bone reaming is required, the procedure may utilize the distal reaming tip 404 to ream holes in obstructive bony structures as previously described. Successful bone reaming may increase overall accessibility to the ligamentum flavum and permit the decompressive procedure to proceed. Step 710 may be optional, e.g., if there are no bony structures impeding needle 322 from reaching the interlaminar space.

At step 712, the bone removal instrument 500 may be inserted into the access portal 302 either after use of the bone reamer instrument 400 by the surgeon or immediately following the retraction of the removable portion from the access portal 302. The bone removal instrument 500 may be advanced through the access portal 302 to a posterior portion of the ligamentum flavum. The surgeon may then actuate the trigger 506 to slide the outer tube 518 along the longitudinal axis 524 to excise tissue and/or bone at the cutting region 520. Subsequently, the soft tissue removal instrument 600 may be inserted for soft tissue removal at step 714. In some embodiments, step 714 is optional, and the entire decompression is performed with only bone removal instrument 500.

As previously described in the present disclosure, it will be appreciated that any of steps 710, 712, and 714 may be performed at the discretion of the operating surgeon. As such, in some procedures, steps 710, 712, and 714 may be performed interchangeably or in any order. Specifically, at least one of step 712 and step 714 may be completed at least once during the procedure to excise a tissue at the target area. However, whether the bone removal instrument 500 is utilized for the excision of bone and/or tissue at step 712 or the soft tissue removal instrument 600 is used for tissue excision at step 714 may depend on the stenotic state of the patient spine and any surrounding structures (i.e., bony structures) preventing a more simplistic removal featuring the sole excision of a soft tissue. In some procedures, the surgeon may elect to perform both step 712 and 714, using both the bone removal instrument 500 and the soft tissue removal instrument 600. In such procedures, the surgeon may perform each of step 712 and 714 only once in the order in which they are sequentially listed. Alternatively, the surgeon may perform these steps in reverse, operating first with the soft tissue removal instrument 600 before using the bone removal instrument 500. Further, the surgeon may use a single excision instrument 500, 600 multiple times within the same procedure, through the access portal, completing one of step 712 and 714 with one of the bone removal instrument 500 and the soft tissue removal instrument 600, respectively, and removing them from the access portal 302 prior to readvancing the same excision instrument 500, 600 as used previously to perform step 712 or 714 for at least an additional removal step.

Regardless of the instrument(s) 500, 600 employed for tissue excision throughout the procedure, the surgery may proceed such that the hypertrophied ligamentum flavum 120' within the stenotic region may be adequately excised to decompress the patient's spine. In some embodiments, excision may involve the actuation of a trigger 506, 606 to engage a cutting region 520, 620 to cut at least one of a tissue or bone. The orientation of the cutting region 520, 620 may be modified by manipulation of an orientation control mechanism 536 to enable ease of cutting based on the location of the hypertrophied ligamentum flavum and/or the surrounding spinal environment. Excised tissue and/or bone may then be removed from the cutting cavity of the 500, 600 using vacuum and/or a push rod assembly as described. If removal of the excised tissue and/or bone from the cutting cavity 522, 622 involves removing the excision instrument 500, 600 from the patient, the excision instrument 500, 600 may be reinserted into the access portal 302 for further cutting within the stenotic region, and step 714 may be repeated until a desired level of tissue excision has occurred. Alternatively, the other excision instrument 500, 600 may be similarly entered into the access portal 302 for further procedural excision purposes. Upon sufficient excision of the hypertrophied ligamentum flavum 120', the excision instrument 500, 600 may undergo one final ejection of excised tissue and/or bone.

Turning now to step 716, the excision instrument may be removed from the access portal 302 following achievement of sufficient decompression of the stenotic area via tissue excision. The surgeon may then close the surgical site by suturing the incision at the back surface of the patient.

Figure 8:
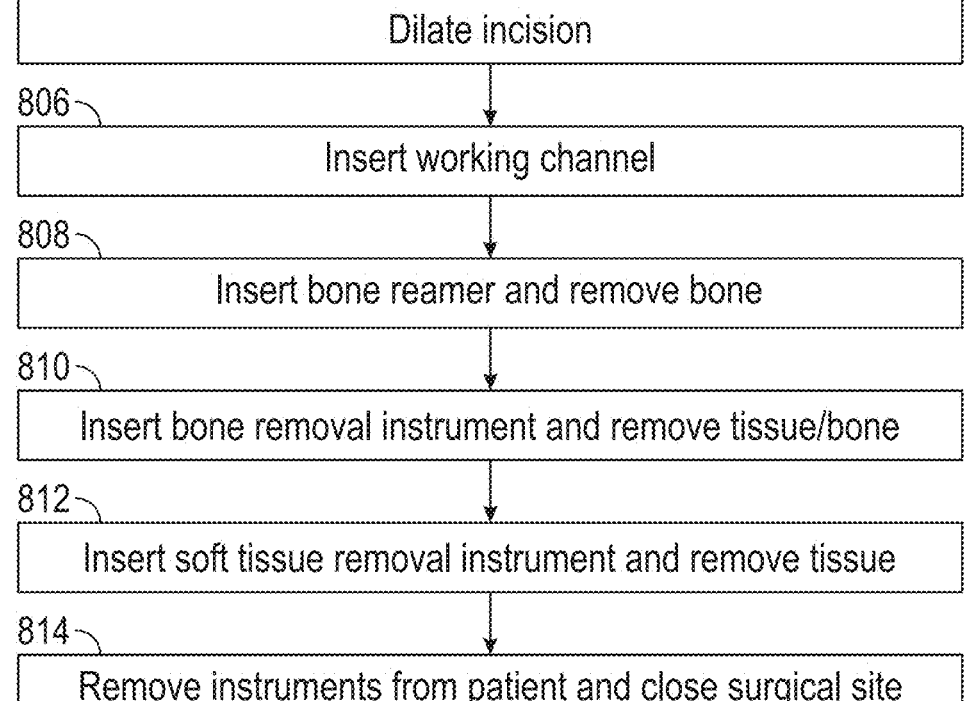
FIG. 8 depicts a method for an open decompression procedure for some embodiments.

FIG. 8 depicts a method 800 for the removal of tissue to decompress the patient spine at a stenotic region. Specifically, this method 800 details the steps that may be used for an open tissue excision procedure.

First, at step 802, the surgeon may create an incision at a back surface of a patient positioned in a prone position. It will be appreciated that the size of the incision required for an open procedure may differ from that of a closed procedure. For instance, for some open procedures a larger incision may be needed to accommodate the various dilators 202 required. In some procedures, this incision may be at least three inches in length.

Once the patient has been properly incised, step 804 may involve the use of a plurality of dilators 202 of increasing diameters to dilate the incision. A first dilator having a first diameter may be inserted into the incision to expand the space to the size of the dilator. In some procedures, an additional dilator of a larger diameter may replace the first dilator within the incision to further expand the space. This step may then be repeated with increasingly larger dilators until the incision has reached a sufficient dilation diameter to accept surgical instruments. In some embodiments, the dilators 202 are inserted over a guidewire that is inserted through the incision.

At step 806, a working channel 204 may be inserted into the dilated incision. This working channel 204 may serve a similar portal-like function as the access portal 302 in the closed decompression procedure. In some embodiments, the working channel 204 may be a sleeve similar in structure to a cylindrical tube; however, it will be appreciated that working channel 204 may be any shape and size providing sufficient passage therethrough for access of the surgical instruments to the target area.

Dilators 202 and/or working channel 204 may be formed of a plastic or metal. In some embodiments, dilators 202 and/or working channel 204 are formed of a clear material so that the surgeon can see through the dilators and/or working channel 204. The working channel 204 may have a diameter in the range of 8 mm, 10 mm, 12 mm, 14 mm, or 16 mm in some embodiments. In some embodiments, dilators 202 and/or working channel 204 is/are configured to be reusable or may be single use.

Subsequent steps 808, 810, 812, and 814 succeeding the insertion of the working channel at step 806 may be substantially similar to the corresponding steps 710, 712, 714, and 716. The difference between the closed decompression and open decompression procedures at these steps may only be noted in their respective uses of an access portal 302 and a working channel 204, respectively, to receive the surgical instruments within. Step 808 may be significantly similar as step 710 such that a bone reamer instrument 400 may be optionally inserted through the working channel 204 and manipulated by the surgeon to remove bone. Likewise, step 810, similarly to step 712, may include inserting a bone removal instrument 500 to excise bone tissue and/or bone through the working channel 204. Steps 812 and 714 may be similar in which the soft tissue removal instrument 600 may be used to excise tissue at the target area. Finally, step 814, involving the removal of the instruments from the working channel 204 and the closing of the surgical site by suturing the incision may be performed by a surgeon in the same manner as step 716.

Features described above as well as those claimed below may be combined in various ways without departing from the scope hereof. The following examples illustrate some possible, non-limiting combinations:

Clause 1. A tissue excision system for treating lumbar spinal stenosis, comprising: an excision instrument comprising: an elongated cutting assembly configured to excise at least one of bone or tissue from the target treatment area comprising a cutting region at the distal end; and an orientation control assembly at a proximal end comprising a knob coupled to a circumference of the elongated cutting assembly such that a rotation of the knob causes a corresponding rotation of the cutting region.

Clause 2. The tissue excision system of clause 1, further comprising: an access instrument configured to provide access to a target treatment area.

Clause 3. The tissue excision system of clause 1 or clause 2, wherein the access instrument comprises: a cannulated shaft comprising an elongated passage therethrough.

Clause 4. The tissue excision system of any of clauses 1-3, wherein the access instrument further comprises: a needle removably inserted through the cannulated shaft to advance the access instrument through a back surface of a patient and to the target treatment area of the patient.

Clause 5. The tissue excision system of any of clauses 1-4, wherein the excision instrument is configured for insertion through the cannulated shaft.

Clause 6. The tissue excision system of any of clauses 1-5, the excision device further comprising: a distal end and a proximal end.

Clause 7. The tissue excision system of any of clauses 1-6, the excision device further comprising: a handle at the proximal end comprising a trigger operable by a user to actuate the cutting region to excise tissue or bone.

Clause 8. The tissue excision system of any of clauses 1-7, wherein the target treatment area is an interlaminar region of the patient.

Clause 9. The tissue excision system of any of clauses 1-8, wherein the cutting region is incrementally rotatable to a plurality of distinct angles.

Clause 10. The tissue excision system of any of clauses 1-9, wherein the cutting region is rotatable without rotating the handle of the excision instrument.

Clause 11. The tissue excision system of any of clauses 1-10, wherein the excision instrument further comprises: a depth control threadedly coupled to an exterior of the orientation control assembly.

Clause 12. The tissue excision system of any of clauses 1-11, wherein the depth control is adjustable along a length of the orientation control assembly to adjust a depth of the cutting region.

Clause 13. The tissue excision system of any of clauses 1-12, further comprising: a bone reamer, comprising: a rod having a rod proximal end and a rod distal end.

Clause 14. The tissue excision system of any of clauses 1-13, the bone reamer further comprising: a cutting tip at the rod distal end.

Clause 15. The tissue excision system of any of clauses 1-14, the bone reamer further comprising: a spring-loaded knob configured to extend the cutting tip anteriorly beyond an initial depth.

Clause 16. The tissue excision system of any of clauses 1-15, wherein the bone reamer further comprises: a housing coupled to the rod proximal end.

Clause 17. The tissue excision system of any of clauses 1-16, the bone reamer housing further comprising: an outer sleeve comprising external threads configured to threadedly engage with internal threads on the spring-loaded knob.

Clause 18. The tissue excision system of any of clauses 1-17, the bone reamer housing further comprising: and a window configured to receive the spring-loaded knob therein.

Clause 19. The tissue excision system of any of clauses 1-18, wherein rotating the spring-loaded knob engages the external threads with the internal threads to extend the cutting tip anteriorly beyond the initial depth.

Clause 20. The tissue excision system of any of clauses 1-19, wherein the elongated cutting assembly further comprises: an outer tube comprising the cutting region.

Clause 21. The tissue excision system of any of clauses 1-20, wherein the cutting region presents a cutting cavity at the outer tube.

Clause 22. The tissue excision system of any of clauses 1-21, wherein the elongated cutting assembly further comprises: a stationary inner tube received within the outer tube.

Clause 23. The tissue excision system of any of clauses 1-22, wherein upon actuation of the trigger, the outer tube slides towards the proximal end along a longitudinal axis of the excision instrument to at least partially enclose the cutting cavity with the stationary inner tube to thereby excise tissue or bone.

Clause 24. The tissue excision system of any of clauses 1-23, wherein the excision instrument further comprises: a stationary inner tube defining a cutting cavity.

Clause 25. The tissue excision system of any of clauses 1-24, the excision instrument further comprising: an outer tube surrounding the stationary inner tube.

Clause 26. The tissue excision system of any of clauses 1-25, wherein when the trigger is actuated, the outer tube slides towards the distal end along a longitudinal axis of the excision instrument to at least partially enclose the cutting cavity with the outer tube.

Clause 27. The tissue excision system of any of clauses 1-26, wherein the cutting region further comprises a plurality of teeth extending from at least one of a front edge, a back edge, or a side edge of the cutting cavity.

Clause 28. A cannulated tissue excision system for treating spinal stenosis, comprising: an excision instrument comprising: an elongated cutting assembly comprising a cutting region at a distal end that is configured to excise at least one of bone or tissue from the interlaminar region; and an orientation control assembly comprising a knob coupled to a circumference of the elongated cutting assembly such that a rotation of the knob causes a corresponding angular orientation of the cutting region.

Clause 29. The cannulated tissue excision system of clause 28, further comprising: an access instrument configured to provide access to an interlaminar region of a patient.

Clause 30. The cannulated tissue excision system of clause 28 or clause 29, wherein the access instrument further comprises: a cannulated access portal.

Clause 31. The cannulated tissue excision system of any of clauses 28-30, wherein the access instrument further comprises: a needle configured to be inserted through the cannulated access portal to advance the access instrument to the interlaminar region.

Clause 32. The cannulated tissue excision system of any of clauses 28-31, wherein the excision instrument is configured to be inserted through the cannulated access portal.

Clause 33. The cannulated tissue excision system of any of clauses 28-32, wherein the excision instrument comprising: a distal end and a proximal end.

Clause 34. The cannulated tissue excision system of any of clauses 28-33, wherein the excision instrument further comprises: a depth control threadedly coupled to the orientation control assembly.

Clause 35. The cannulated tissue excision system of any of clauses 28-34, wherein the depth control is adjustable longitudinally along the orientation control assembly to control a depth of the cutting region within the patient.

Clause 36. The cannulated tissue excision system of any of clauses 28-35, wherein the access instrument further comprises: a backstop coupled to a circumference of the cannulated access portal.

Clause 37. The cannulated tissue excision system of any of clauses 28-36, wherein the backstop is adjustable along a length thereof to control a depth of the cannulated access portal by abutting a back surface of the patient.

Clause 38. The cannulated tissue excision system of any of clauses 28-37, wherein the backstop further comprises: grooves disposed radially about a circumference of the backstop to provide a gripping aid for a user.

Clause 39. The cannulated tissue excision system of any of clauses 28-38, wherein the excision instrument further comprises: a stationary inner tube.

Clause 40. The cannulated tissue excision system of any of clauses 28-39, a removable solid plunger rod received within the stationary inner tube Clause 41. The cannulated tissue excision system of any of clauses 28-40, wherein the removable solid plunger rod is configured to slide distally within the stationary inner tube toward the distal end to eject at least one of an excised tissue or an excised bone from the cutting region.

Clause 42. The cannulated tissue excision system of any of clauses 28-41, wherein the excision instrument further comprises: a suction port at the proximal end of the excision instrument Clause 43. The cannulated tissue excision system of any of clauses 28-42, wherein the suction port is configured to be coupled to a vacuum for removal of at least one of an excised tissue or an excised bone from the elongated cutting assembly while the excision instrument remains within the cannulated access portal of the access instrument.

Clause 44. The cannulated tissue excision system of any of clauses 28-43, wherein the cutting region further comprises: an arcuate cutting tip.

Clause 45. The cannulated tissue excision system of any of clauses 28-44, wherein the arcuate cutting tip further comprises: a distal groove configured to be viewable under fluoroscopy.

Clause 46. The cannulated tissue excision system of any of clauses 28-45, wherein the cutting region further comprises a plurality of teeth aligned in a linear configuration and extending from at least one of a front edge, a back edge, or a side edge of the cutting cavity.

Clause 47. A method for treating spinal stenosis, comprising: providing an excision instrument comprising: an elongated cutting assembly comprising a cutting region; an orientation control assembly comprising: a knob coupled to a circumference of the elongated cutting assembly; and a trigger coupled to the elongated cutting assembly.

Clause 48. The method of clause 47, further comprising: providing an access instrument comprising: an access portal comprising a cannula, the cannula further comprising: a shaft with an outer circumference; and an elongated passage through the shaft.

Clause 49. The method of clause 47 or clause 48, further comprising: rotating the knob to adjust an angular orientation of the cutting region.

Clause 50. The method of any of clauses 47-49, further comprising: advancing the access instrument into a patient and to a target area.

Clause 51. The method of any of clauses 47-50, further comprising: inserting the excision instrument through the elongated passage of the access instrument to the target area.

Clause 52. The method of any of clauses 47-51, further comprising: actuating the trigger to excise at least one of tissue or bone at the cutting region.

Clause 53. The method of any of clauses 47-52, wherein the elongated cutting assembly further comprises: a distal end.

Clause 54. The method of any of clauses 47-53, wherein the elongated cutting assembly further comprises: a cutting cavity.

Clause 55. The method of any of clauses 47-54, wherein the elongated cutting assembly further comprises: an outer tube.

Clause 56. The method of any of clauses 47-55, wherein pushing the trigger toward the distal end extends the cutting cavity to a distal most position and maintains the cutting cavity in a fully opened configuration.

Clause 57. The method of any of clauses 47-56, further comprising: providing a backstop comprising a distal end.

Clause 58. The method of any of clauses 47-57, wherein the backstop further comprises: a biasing mechanism to detachably couple the backstop to the outer circumference of the shaft.

Clause 59. The method of any of clauses 47-58, further comprising: adjusting the backstop to a desired position along the outer circumference of the shaft.

Clause 60. The method of any of clauses 47-59, further comprising: abutting the distal end of the backstop with a back surface of the patient to control a depth of the excision instrument.

Clause 61. The method of any of clauses 47-60, further comprising: attaching a suction attachment to a connection port at a proximal end of the excision instrument.

Clause 62. The method of any of clauses 47-61, further comprising: suctioning at least one of tissue or bone excised at the cutting region from the elongated cutting assembly.

Clause 63. The method of any of clauses 47-62, wherein rotating the knob to selectively control the angular orientation of the cutting region further comprises: rotating the cutting region to at least one of a plurality of angles between 0 and 360 degrees.

Clause 64. The method of any of clauses 47-63, wherein rotating the cutting region does not involve a rotation of a handle of the excision instrument.

Clause 65. The method of any of clauses 47-64, wherein the cutting region further comprises teeth extending from at least one of a front edge, a back edge, or a side edge.

Clause 66. The method of any of clauses 47-65, wherein the teeth grip the surrounding tissue to prevent slippage during excision.

Although the present disclosure has been described with reference to the embodiments illustrated in the attached drawing figures, it is noted that equivalents may be employed, and substitutions made herein without departing from the scope of the present disclosure as recited in the claims.

Having thus described various embodiments of the present disclosure, what is claimed as new and desired to be protected by Letters Patent includes the following:

1. A tissue excision system for treating lumbar spinal stenosis, comprising:
an access instrument configured to provide access to a target treatment area, comprising:
a cannulated shaft comprising an elongated passage therethrough; and
a needle removably inserted through the cannulated shaft to advance the access instrument through a back surface of a patient and to the target treatment area of the patient; and
an excision instrument configured to be inserted through the cannulated shaft, comprising:
a distal end and a proximal end;
an elongated cutting assembly configured to excise at least one of bone or tissue from the target treatment area and comprising a cutting region at the distal end and further comprising:
a stationary inner tube;
a solid plunger rod received within the stationary inner tube and configured to slide distally within the stationary inner tube toward the distal end to eject at least one of an excised tissue or an excised bone from the cutting region;
a handle at the proximal end comprising a trigger operable by a user to actuate the elongated cutting assembly to excise tissue or bone at the cutting region; and
an orientation control assembly at the proximal end comprising a knob coupled to a circumference of the elongated cutting assembly such that a rotation of the knob causes a corresponding rotation of the cutting region.

2. The tissue excision system of claim 1, wherein the target treatment area is an interlaminar region of the patient.

3. The tissue excision system of claim 1, wherein the cutting region is incrementally rotatable to a plurality of distinct angles.

4. The tissue excision system of claim 3, wherein the cutting region is rotatable without rotating the handle of the excision instrument.

5. The tissue excision system of claim 1, wherein the excision instrument further comprises:
a depth control adjustable along a length of the excision instrument to adjust a depth of the cutting region.

6. The tissue excision system of claim 1, further comprising:
a bone reamer, comprising:
a rod having a rod proximal end and a rod distal end; and
a cutting tip at the rod distal end, wherein the cutting tip is adjustable longitudinally to adjust a depth of the cutting tip.

7. The tissue excision system of claim 6, wherein the bone reamer further comprises:
a bone reamer knob having internal threads; and a housing coupled to the rod proximal end, comprising:
    an outer sleeve comprising external threads configured to threadedly engage with the internal threads on the knob; and
    a window configured to receive the knob therein, wherein rotating the knob engages the external threads with the internal threads to extend the cutting tip anteriorly beyond an initial depth.

8. The tissue excision system of claim 1, wherein the elongated cutting assembly further comprises:
    an outer tube comprising the cutting region, the cutting region presenting a cutting cavity; and
    a stationary solid shaft received within the outer tube,
    wherein when the trigger is actuated, the outer tube slides towards the proximal end along a longitudinal axis of the excision instrument to at least partially enclose the cutting cavity with the stationary solid shaft to thereby excise tissue or bone.

9. The tissue excision system of claim 1, wherein the excision instrument further comprises:
    a cutting tip at the distal end, the cutting tip comprising teeth configured to grab and hold tissue during cutting.

10. A tissue excision system for treating spinal stenosis, comprising:
    an access instrument configured to provide access to an interlaminar region of a patient, comprising:
    a cannulated access portal; and
    a needle configured to be inserted through the cannulated access portal to advance the access instrument to the interlaminar region;
    an excision instrument configured to be inserted through the cannulated access portal, the excision instrument comprising:
        a distal end and a proximal end;
        an elongated cutting assembly comprising a cutting region at the distal end that is configured to excise at least one of bone or tissue from the interlaminar region and further comprising:
            a stationary inner tube;
            a solid plunger rod received within the stationary inner tube and configured to slide distally within the stationary inner tube toward the distal end to eject at least one of an excised tissue or an excised bone from the cutting region;
        an orientation control assembly comprising a knob coupled to a circumference of the elongated cutting assembly such that a rotation of the knob causes a corresponding angular orientation of the cutting region; and
        a depth control that is adjustable longitudinally along the elongated cutting assembly to control a depth of the cutting region within the patient.

11. The tissue excision system of claim 10, wherein the circumference is a first circumference and wherein the access instrument further comprises:
    a backstop coupled to a second circumference of the cannulated access portal and adjustable along a length thereof to control a depth of the cannulated access portal by abutting a back surface of the patient.

12. The tissue excision system of claim 11, wherein the backstop further comprises:
    grooves disposed radially about a third circumference of the backstop to provide a gripping aid for a user.

13. The tissue excision system of claim 10, wherein the cutting region further comprises:

an arcuate cutting tip comprising a distal groove configured to be viewable under fluoroscopy.

14. The tissue excision system of claim 10, further comprising a bone reamer.

15. The tissue excision system of claim 10, wherein the solid plunger rod comprises an external diameter that substantially matches an inner diameter of the stationary inner tube.

16. The tissue excision system of claim 10, wherein the cutting region comprises:
    an inner shaft having a distal cutting end, comprising:
        an upper portion; and
        a lower portion, wherein the lower portion is angled relative to the upper portion.

17. A method for treating spinal stenosis, comprising:
    providing an access instrument comprising:
        an access portal comprising a cannula, the cannula further comprising:
            a shaft with an outer circumference; and
            an elongated passage through the shaft;
    providing an excision instrument comprising:
        an elongated cutting assembly comprising a cutting region, comprising:
            a stationary inner tube;
            a solid plunger rod received within the stationary inner tube;
        an orientation control assembly comprising:
            a knob coupled to a circumference of the elongated cutting assembly; and
            a trigger coupled to the elongated cutting assembly;
    advancing the access instrument into a patient and to a target area;
    inserting the excision instrument through the elongated passage of the access instrument to the target area;
    rotating the knob to adjust an angular orientation of the cutting region;
    actuating the trigger to excise at least one of tissue or bone at the cutting region; and
    sliding the solid plunger rod distally within the stationary inner tube toward a distal end of the excision instrument to eject at least one of an excised tissue or an excised bone from the cutting region.

18. The method of claim 17, wherein the elongated cutting assembly further comprises:
    a cutting cavity at the distal end; and
    an outer tube,
    wherein pushing the trigger toward the distal end extends the cutting cavity to a distal most position and maintains the cutting cavity in a fully opened configuration.

19. The method of claim 17, further comprising:
    providing a backstop comprising a backstop distal end and a biasing mechanism to detachably couple the backstop to the outer circumference of the shaft;
    adjusting the backstop to a desired position along the outer circumference of the shaft; and
    abutting the backstop distal end with a back surface of the patient to control a depth of the excision instrument.

20. The method of claim 17, wherein rotating the knob to selectively control the angular orientation of the cutting region further comprises:
    rotating the cutting region to at least one of a plurality of angles between 0 and 360 degrees,
    wherein rotating the cutting region does not involve a rotation of a handle of the excision instrument.

* * * * *